US008889375B2

(12) United States Patent
Isa et al.

(10) Patent No.: US 8,889,375 B2
(45) Date of Patent: Nov. 18, 2014

(54) HYPOGLYCEMIC EFFECT ENHANCER (75) Inventors: Yasuhiro Isa, Hyogo (JP); Masaki Shimakawa, Hyogo (JP); Hiroshi Ohno, Hyogo (JP); Hideki Yamamura, Hyogo (JP)

(73) Assignee: Biofermin Pharmaceutical Co., Ltd., Hyogo (JP)

( * ) Notice: Subject to any disclaimer, the term of this patent is extended or adjusted under 35 U.S.C. 154(b) by 465 days.

(21) Appl. No.: 13/258,064

(22) PCT Filed: Mar. 25, 2010

(86) PCT No.: PCT/JP2010/055238
§ 371 (c)(1),
(2), (4) Date: Sep. 28, 2011

(87) PCT Pub. No.: WO2010/110374
PCT Pub. Date: Sep. 30, 2010

(65) Prior Publication Data
US 2012/0014923 A1 Jan. 19, 2012

(30) Foreign Application Priority Data
Mar. 26, 2009 (JP) .................. 2009-077555

(51) Int. Cl.
*C12N 15/09* (2006.01)
*A23L 2/02* (2006.01)
*A61K 35/74* (2006.01)
*A61K 45/06* (2006.01)
*A61K 31/133* (2006.01)
*C07C 215/44* (2006.01)
*A23L 1/03* (2006.01)
*C07D 211/46* (2006.01)
*A23L 1/30* (2006.01)
*A61K 31/702* (2006.01)
*A61K 31/445* (2006.01)

(52) U.S. Cl.
CPC .............. *A61K 31/133* (2013.01); *A23L 2/02* (2013.01); *A61K 35/742* (2013.01); *A23Y 2300/00* (2013.01); *A23Y 2240/33* (2013.01); *A61K 45/06* (2013.01); *C07C 215/44* (2013.01); *A23V 2002/00* (2013.01); *A23Y 2300/25* (2013.01); *A61K 35/744* (2013.01); *A23L 1/0345* (2013.01); *C07D 211/46* (2013.01); *A23L 1/3014* (2013.01); *A61K 31/702* (2013.01); *A61K 35/747* (2013.01); *A61K 31/445* (2013.01)
USPC ....................... 435/69.2; 435/7.32

(58) Field of Classification Search
CPC ................................................. A61K 2300/00
USPC ................................................. 435/69.2, 7.32
See application file for complete search history.

(56) References Cited

U.S. PATENT DOCUMENTS

2009/0148545 A1 6/2009 Falk et al.

FOREIGN PATENT DOCUMENTS

| EP | 0 194 794 | 9/1986 |
|---|---|---|
| JP | 61-205215 | 9/1986 |
| JP | 7-2647 | 1/1995 |
| JP | 10-007577 | 1/1998 |
| JP | 2006-020606 | 1/2006 |
| JP | 2007-330124 | 12/2007 |
| JP | 2008-222701 | 9/2008 |
| WO | 2007/140230 | 12/2007 |
| WO | 2008/093670 | 8/2008 |

OTHER PUBLICATIONS

Hong et al. "Rapid identification of bifidobacteria in dairy products by gene-targeted species-specific PCR technique and DGGE", Asian-Aust. J. Anim. Sci., 200720(12):1887-1894.*
Kwon et al. "Anti-diabetes functionality of kefir culture-mediated fermented soymilk supplement with *Rhodiola* extracts", Food Biotechnology, 2006, 20(1):13-29.*
Hong et al. "Rapid identification of bifidobacteria in dairy products by gene-targeted species-specific PCR technique and DGGE", Asian-Aust. J. Anim. Sci., 2007, 20(12):1887-1894.*
Translation pp. 1-16 of : Narimiya et al. "Combinational effect of acarbose and *Lactobacillus* preparation in improving intestinal bacterial flora and abdominal symptoms", Rinsho to Kenkyo, 83(8):1249-1254.*
English translation of the International Preliminary Report on Patentability and Written Opinion dated Oct. 18, 2011.
M. Narumiya et al., "Combinational Effect of Acarbose and *Lactobacillus* Preparation in Improving Intestinal Bacterial Flora and Abdominal Symptoms", Japanese Journal of Clinical and Experimental Medicine, vol. 83, No. 8, pp. 1249-1254, Aug. 2006 with English translation.
T. Matsui et al., "In Vitro Survey of α-Glucosidase Inhibitory Food Components", Bioscience, Biotechnology, and Biochemistry, vol. 60, No. 12, pp. 2019-2022, 1996.

\* cited by examiner

*Primary Examiner* — Bin Shen
(74) *Attorney, Agent, or Firm* — Wenderoth, Lind & Ponack, L.L.P.

(57) ABSTRACT

A hypoglycemic effect enhancer for enhancing the activity of an α-glucosidase inhibitor, the enhancer comprising at least one kind of bacteria selected from the group consisting of bifidobacteria, lactic acid bacteria, saccharifying bacteria, and butyric acid bacteria.

3 Claims, 4 Drawing Sheets

HYPOGLYCEMIC EFFECT ENHANCER

This application is a U.S. national stage of International Application No. PCT/JP2010/055238 filed Mar. 25, 2010.

TECHNICAL FIELD

The present invention relates to a hypoglycemic effect enhancer, which enhances the hypoglycemic activity of a hypoglycemic drug.

BACKGROUND ART

In recent years, due to changes in living environment, patients or potential patients with lifestyle-related diseases (adult diseases), such as diabetes and obesity, have been increasing in number. For example, diabetes is a disease caused by abnormal saccharometabolism, and is a disease involving the risk of various distinctive complications resulting from pathologically elevated blood glucose level (glucose concentration in the blood). Dietary therapy is essential in the treatment of diabetes. However, when dietary therapy alone is not sufficiently effective, insulin or an oral hypoglycemic drug is used.

An α-glucosidase (disaccharide-degrading enzyme) inhibitor, which is one of oral hypoglycemic drugs, has an activity of delaying degradation of disaccharides to monosaccharides and absorption thereof, and therefore is capable of inhibiting postprandial rise in blood glucose level by delaying intestinal digestion and absorption of saccharides, such as starch. However, such an α-glucosidase inhibitor is not effective in the treatment of high blood glucose level not after eating, and incapable of decreasing fasting blood glucose level. Therefore, enhancement of the hypoglycemic activity of such a hypoglycemic drug has been desired. In addition, α-glucosidase inhibitors have strong side effects including meteorism, feeling of fullness, abdominal discomfort, and diarrhea.

Patent Literature 1 discloses a saccharide digestion inhibitory agent comprising a combination of an α-glucosidase inhibitor and nonpathogenic lactic acid-producing viable cells, and a saccharide digestion inhibitory composition comprising the same. Patent Literature 1 describes that the combination of an α-glucosidase inhibitor and lactic acid-producing viable cells was effective in preventing diarrhea etc. Non Patent Literature 1 discloses that concomitant administration of acarbose and a lactic acid bacterium *Lactobacillus casei* YIT9029 improved side effects of acarbose, such as abdominal fullness. Patent Literature 2 and 3 disclose a health food composition comprising an ingredient with α-glucosidase inhibitory activity and an ingredient with intestinal environment-improving activity, lactic acid bacteria for example, as a health food composition having no risk of side effects and usable for preventing or improving obesity and lifestyle-related diseases, such as diabetes. In Patent Literature 2 and 3, it is stated that since the composition comprising an ingredient with intestinal environment-improving activity, lactic acid bacteria for example, inhibits intestinal decomposition, promotes regular bowel movement, and prevents constipation, the composition is promising for decreasing obesity and preventing colorectal cancer. Patent Literature 4 discloses a hypoglycemic drug comprising lactic acid bacterial cells as an active ingredient.

However, Patent Literature 1 to 4 and Non Patent Literature 1 have no description regarding enhancement of the activity of the hypoglycemic drugs. Therefore, there is room for improvement to achieve a better hypoglycemic activity useful for prevention or treatment of lifestyle-related diseases, such as diabetes and obesity.

CITATION LIST

Patent Literature

[PTL 1] JP 07-2647 B
[PTL 2] JP 2007-330124 A
[PTL 3] JP 2006-20606 A
[PTL 4] JP 10-7577 A

Non Patent Literature

[NPL 1] Manabu Narumiya et al., "Combinational effect of acarbose and *Lactobacillus* preparation in improving intestinal bacterial flora and abdominal symptoms", Rinsho to Kenkyu, vol. 83, No. 8, 149-154 2006

SUMMARY OF INVENTION

Technical Problem

In the circumstances set forth above, an object of the present invention is to provide a hypoglycemic effect enhancer, which efficiently enhances the hypoglycemic activity of a hypoglycemic drug.

Solution to Problem

The present inventors made extensive investigations to solve the problem described above, and examined the hypoglycemic activity of various substances. As a result, the inventors found that administration of an α-glucosidase inhibitor and bacteria, such as lactic acid bacteria, to an animal produces specific synergy of the α-glucosidase inhibitor and the bacteria, such as lactic acid bacteria, and thereby significantly decreases the blood glucose level (glucose concentration in the blood) in the fasting state. It was newly found that while single-substance administration of an α-glucosidase inhibitor or bacteria, such as lactic acid bacteria, does not significantly decrease the blood glucose level, concomitant administration of the α-glucosidase inhibitor and the bacteria, such as lactic acid bacteria, synergistically enhances the hypoglycemic activity in the fasting state.

Further, the inventors found that, even in the oral glucose tolerance test (OGTT) where glucose, which is a monosaccharide, is administered orally, concomitant administration of the α-glucosidase inhibitor and the bacteria, such as lactic acid bacteria, synergistically enhances the hypoglycemic activity and significantly decreases the blood glucose level. However, single-substance administration of the α-glucosidase inhibitor or the bacteria, such as lactic acid bacteria, hardly decreased the blood glucose level in the OGTT. Based on the findings, the inventors found that administration of an α-glucosidase inhibitor in combination with bacteria, such as lactic acid bacteria, synergistically enhances the hypoglycemic activity.

Since there seems to be relatively little disaccharide in the digestive tract in the fasting state as compared with in the postprandial state, and glucose, which is a monosaccharide, is administered in the OGTT, it is reasonable to consider that the excellent hypoglycemic activity achieved in the case of concomitant use of an α-glucosidase inhibitor and bacteria, such as lactic acid bacteria, is not resulting from enhancement of the disaccharide-degrading activity of the α-glucosidase inhibitor but resulting from synergistic enhancement of the hypoglycemic activity in the fasting state and in the glucose loaded state, the synergistic enhancement first achieved by the concomitant use of an α-glucosidase inhibitor and bacteria, such as lactic acid bacteria. The inventors also found that in such administration of an α-glucosidase inhibitor in combination with bacteria, such as lactic acid bacteria, even when the amount of the α-glucosidase inhibitor is less than usual, effective decrease in the blood glucose level in both the fasting state and the glucose loaded state can be achieved. This finding led the inventers to conceive of efficient enhancement of the hypoglycemic activity with reduced side effects.

Further, according to "Development of BASEN Tablets (trade name) 3. Effects on insulin secretion and pancreatic islet lesions" by Takeda Pharmaceutical Company Ltd. (www2.takedamed.com/content/search/doc1/067/kaihatsu/kai067_4.html), 9-week dietary administration (0.005%: 4.1 mg/kg·day) of voglibose, which is an α-glucosidase inhibitor, to GK rats characterized by abnormal glucose tolerance improved the glucose tolerance. The inventers found that while 6-week dietary administration (0.0003%: 0.6 mg/kg·day) of voglibose to KK-$A^y$ mice having abnormal glucose tolerance did not improve the glucose tolerance, 6-week administration of the diet to which at least one kind of bacteria selected from the group consisting of bifidobacteria, lactic acid bacteria, saccharifying bacteria, and butyric acid bacteria was added improved the glucose tolerance. As a result, it was shown that concomitant administration of an α-glucosidase inhibitor and bacteria, such as lactic acid bacteria, is more effective, even when a reduced amount of the α-glucosidase inhibitor is administered for a shorter period, in achieving hypoglycemic effect than single-substance administration of the α-glucosidase inhibitor.

Based on the above findings, the inventors conducted further research and completed the present invention.

That is, the present invention relates to the following (1) to (18).

(1) A hypoglycemic effect enhancer for enhancing the activity of an α-glucosidase inhibitor, the enhancer comprising at least one kind of bacteria selected from the group consisting of bifidobacteria, lactic acid bacteria, saccharifying bacteria, and butyric acid bacteria.

(2) The hypoglycemic effect enhancer according to the above (1), further comprising an α-glucosidase inhibitor.

(3) The hypoglycemic effect enhancer according to the above (1) or (2), wherein the α-glucosidase inhibitor is a valiolamine derivative represented by the general formula (I):

(wherein A represents a chain hydrocarbon group having 1 to 10 carbon atoms and optionally having one or more of hydroxyl, phenoxy, thienyl, furyl, pyridyl, cyclohexyl, and optionally substituted phenyl; a cyclic hydrocarbon group having 5 or 6 carbon atoms and optionally having one or more of hydroxyl, hydroxymethyl, methyl, and amino; or a sugar residue), an N-substituted valienamine derivative represented by the general formula (II):

(wherein A has the same meaning as defined above),
an N-substituted validamine derivative represented by the general formula (III):

(wherein A has the same meaning as defined above), or a 3,4,5-trihydroxypiperidine represented by the general formula (IV):

(wherein $R^1$ and $R^3$ may be the same or different and independently represent a hydrogen atom, an optionally substituted linear, branched, or cyclic, saturated or unsaturated aliphatic hydrocarbon group, or an optionally substituted hydrocarbon ring, aromatic ring, or hetero ring; $R^2$ represents —H, —OH, —OR', —SH, —SR', —NH$_2$, —NHR', (R')(R''), NH$_2$CH$_2$—, NHR'—CH$_2$—, NR'R''—CH$_2$—, —COOH, —COOR', HO—CH$_2$—, R'CO—NHCH$_2$—, R'—NR''CH$_2$—, R'SO$_2$NHCH$_2$—, R'SO$_2$—NR''CH$_2$—, R'—NH—CO—NH—CH$_2$—, R'—NH—CS—NH—CH$_2$—R'—O—CO—NH—CH$_2$—, —SO$_3$H, —CN, —CONH$_2$, —CONHR', or —CONR'R'', wherein R' and R'' may be the same or different and each have the same meaning as that of $R^1$; and when $R^3$ is —CH$_2$OH and $R^2$ is a hydrogen atom or —OH, when $R^3$ is a hydrogen atom and $R^2$ is a hydrogen atom, —OH, —SO$_3$H, —CN, or —CH$_2$—NH$_2$, or when $R^3$ is —CH$_2$—NH$_2$ and $R^2$ is —OH, $R^1$ is not a hydrogen atom).

(4) A hypoglycemic effect enhancer for enhancing the activity of at least one kind of bacteria selected from the group consisting of bifidobacteria, lactic acid bacteria, saccharifying bacteria, and butyric acid bacteria, the enhancer comprising an α-glucosidase inhibitor.

(5) The hypoglycemic effect enhancer according to the above (4), further comprising at least one kind of bacteria selected from the group consisting of bifidobacteria, lactic acid bacteria, saccharifying bacteria, and butyric acid bacteria.

(6) The hypoglycemic effect enhancer according to the above (4) or (5), wherein the α-glucosidase inhibitor is a valiolamine derivative represented by the general formula (I), an N-substituted valienamine derivative represented by the general formula (II), an N-substituted validamine derivative represented by the general formula (III), or a 3,4,5-trihydroxypiperidine represented by the general formula (IV).

(7) A pharmaceutical drug comprising the hypoglycemic effect enhancer according to any one of the above (1) to (6).

(8) A food or drink composition for enhancing the hypoglycemic activity of an α-glucosidase inhibitor, the composition comprising the hypoglycemic effect enhancer according to any one of the above (1) to (3).

(9) A food or drink composition for enhancing the hypoglycemic activity of at least one kind of bacteria selected from the group consisting of bifidobacteria, lactic acid bacteria, saccharifying bacteria, and butyric acid bacteria, the composition comprising the hypoglycemic effect enhancer according to any one of the above (4) to (6).

(10) Use of at least one kind of bacteria selected from the group consisting of bifidobacteria, lactic acid bacteria, saccharifying bacteria, and butyric acid bacteria, for enhancing the hypoglycemic activity of an α-glucosidase inhibitor.

(11) Use of an α-glucosidase inhibitor, for enhancing the hypoglycemic activity of at least one kind of bacteria selected from the group consisting of bifidobacteria, lactic acid bacteria, saccharifying bacteria, and butyric acid bacteria.

(12) An expression promoter for the hypoglycemic activity of an α-glucosidase inhibitor, the promoter comprising at least one kind of bacteria selected from the group consisting of bifidobacteria, lactic acid bacteria, saccharifying bacteria, and butyric acid bacteria.

(13) At least one kind of bacteria selected from the group consisting of bifidobacteria, lactic acid bacteria, saccharifying bacteria, and butyric acid bacteria, for enhancing the hypoglycemic activity of an α-glucosidase inhibitor.

(14) An α-glucosidase inhibitor for enhancing the hypoglycemic activity of at least one kind of bacteria selected from the group consisting of bifidobacteria, lactic acid bacteria, saccharifying bacteria, and butyric acid bacteria.

(15) At least one kind of bacteria selected from the group consisting of bifidobacteria, lactic acid bacteria, saccharifying bacteria, and butyric acid bacteria, for promoting the expression of the hypoglycemic activity of an α-glucosidase inhibitor.

(16) A method for enhancing the hypoglycemic activity of an α-glucosidase inhibitor, the method comprising administering to an animal at least one kind of bacteria selected from the group consisting of bifidobacteria, lactic acid bacteria, saccharifying bacteria, and butyric acid bacteria in combination with an α-glucosidase inhibitor.

(17) A method for enhancing the hypoglycemic activity of at least one kind of bacteria selected from the group consisting of bifidobacteria, lactic acid bacteria, saccharifying bacteria, and butyric acid bacteria, the method comprising administering to an animal an α-glucosidase inhibitor in combination with the bacteria.

(18) A method for promoting the expression of the hypoglycemic activity of an α-glucosidase inhibitor, the method comprising administering to an animal at least one kind of bacteria selected from the group consisting of bifidobacteria, lactic acid bacteria, saccharifying bacteria, and butyric acid bacteria in combination with an α-glucosidase inhibitor.

The present invention also includes use of at least one kind of bacteria selected from the group consisting of bifidobacteria, lactic acid bacteria, saccharifying bacteria, and butyric acid bacteria, for preparing a hypoglycemic effect enhancer which enhances the activity of an α-glucosidase inhibitor;

use of an α-glucosidase inhibitor for preparing a hypoglycemic effect enhancer which enhances the activity of at least one kind of bacteria selected from the group consisting of bifidobacteria, lactic acid bacteria, saccharifying bacteria, and butyric acid bacteria; and use of at least one kind of bacteria selected from the group consisting of bifidobacteria, lactic acid bacteria, saccharifying bacteria, and butyric acid bacteria, for preparing an expression promoter for the hypoglycemic activity of an α-glucosidase inhibitor.

Advantageous Effects of Invention

The hypoglycemic effect enhancer of the present invention is capable of synergistically enhancing the hypoglycemic activity of a hypoglycemic drug, and therefore is effective in preventing or improving lifestyle-related diseases, such as diabetes and obesity. In addition, due to the synergistically enhanced hypoglycemic activity of the hypoglycemic drug, the dosage amount can be reduced, and therefore side effects of the hypoglycemic drug can also be decreased. Further, even when the α-glucosidase inhibitor is administered in a less amount for a shorter period than usual, an excellent hypoglycemic effect can be achieved.

DESCRIPTION OF EMBODIMENTS

The first aspect of the hypoglycemic effect enhancer of the present invention (hereinafter may be simply referred to as "the hypoglycemic effect enhancer of the present invention 1") is a hypoglycemic effect enhancer for enhancing the activity of an α-glucosidase inhibitor, the enhancer comprising at least one kind of bacteria selected from the group consisting of bifidobacteria, lactic acid bacteria, saccharifying bacteria, and butyric acid bacteria. The comprised bacteria serve to enhance the hypoglycemic activity of an α-glucosidase inhibitor. The hypoglycemic effect enhancer of the present invention 1 preferably further comprises an α-glucosidase inhibitor.

The second aspect of the hypoglycemic effect enhancer of the present invention (hereinafter may be simply referred to as "the hypoglycemic effect enhancer of the present invention 2") is a hypoglycemic effect enhancer for enhancing the activity of at least one kind of bacteria selected from the group consisting of bifidobacteria, lactic acid bacteria, saccharifying bacteria, and butyric acid bacteria, the enhancer comprising an α-glucosidase inhibitor. The comprised α-glucosidase inhibitor serves to enhance the hypoglycemic activity of the bacteria. The hypoglycemic effect enhancer of the present invention 2 preferably further comprises at least one kind of bacteria selected from the group consisting of bifidobacteria, lactic acid bacteria, saccharifying bacteria, and butyric acid bacteria.

In the hypoglycemic effect enhancer of the present invention 1 and the hypoglycemic effect enhancer of the present invention 2 (hereinafter these may be simply referred to as "the hypoglycemic effect enhancer of the present invention"), use of at least one kind of bacteria selected from the group consisting of bifidobacteria, lactic acid bacteria, saccharifying bacteria, and butyric acid bacteria in combination with an α-glucosidase inhibitor specifically and synergistically enhances the hypoglycemic activity of the bacteria and/or the α-glucosidase inhibitor and thereby can exert an excellent hypoglycemic activity. Therefore, with use of the hypoglycemic effect enhancer of the present invention, lifestyle-related diseases, such as diabetes and obesity, can be efficiently prevented or improved. In such use of an α-glucosidase inhibitor in combination with the above-mentioned bacteria, even when the amount of the α-glucosidase inhibitor is less than usual, effective decrease in the blood glucose level can be achieved. As a result, the hypoglycemic activity can be efficiently enhanced with reduced side effects. Further, even when the amount of the α-glucosidase inhibitor is less than the usual amount (the amount usually used in single-substance administration) aiming for the hypoglycemic effect, an excellent hypoglycemic effect can be achieved in a shorter period.

As used herein, "prevention" includes controlling or delaying the onset. Also, "improvement" includes not only completely curing symptoms or diseases but also alleviating symptoms.

The hypoglycemic effect enhancer of the present invention will be described in more detail.

The α-glucosidase inhibitor used in the present invention is preferably a valiolamine derivative represented by the general formula (I):

(I)

(wherein A represents a chain hydrocarbon group having 1 to 10 carbon atoms and optionally having one or more of hydroxyl, phenoxy, thienyl, furyl, pyridyl, cyclohexyl, and optionally substituted phenyl; a cyclic hydrocarbon group having 5 or 6 carbon atoms and optionally having one or more of hydroxyl, hydroxymethyl, methyl, and amino; or a sugar residue), which is described in, for example, JP 57-200335 A, JP 58-59946 A, JP 58-162597 A, JP 58-216145 A, JP 59-73549 A, JP 59-95297 A, JP 7-2647 B, and JP 11-236337 A.

In the above general formula (I), the A includes, for example, linear or branched, saturated or unsaturated aliphatic hydrocarbon groups having 1 to 10 carbon atoms, and the optionally substituted phenyl group includes a phenyl group optionally substituted with, for example, lower alkyl, lower alkoxy, halogen, phenyl, etc.

The sugar residue means a remaining group obtained by removing a hydrogen atom from a saccharide molecule, and includes for example, sugar residues derived from monosaccharides and oligosaccharides.

Specific examples of the N-substituted valiolamine derivative represented by the above general formula (I) include
(1) N-phenethyl valiolamine,
(2) N-(3-phenylallyl)valiolamine,
(3) N-furfuryl valiolamine,
(4) N-thienyl valiolamine,
(5) N-(3-pyridyl methyl)valiolamine,
(6) N-(4-bromobenzyl)valiolamine,
(7) N—[(R)-β-hydroxy phenethyl]valiolamine,
(8) N—[(S)-β-hydroxy phenethyl]valiolamine,
(9) N-(β-hydroxy-2-methoxy phenethyl)valiolamine,
(10) N-(3,5-di-tert-butyl-4-hydroxybenzyl)valiolamine,
(11) N-(cyclohexyl methyl)valiolamine,
(12) N-geranyl valiolamine,
(13) N-(1,3-dihydroxy-2-propyl)valiolamine,
(14) N-(1,3-dihydroxy-1-phenyl-2-propyl)valiolamine,
(15) N—[(R)-α-(hydroxymethyl)benzyl]valiolamine,
(16) N-cyclohexyl valiolamine,
(17) N-(2-hydroxy cyclohexyl)valiolamine,
(18) N-[(1R,2R)-2-hydroxy cyclohexyl]valiolamine,
(19) N-(2-hydroxy cyclopentyl)valiolamine,
(20) Methyl 4-[(1S,2S)-(2,4,5(OH)/3,5)-2,3,4,5-tetrahydroxy-5-(hydroxymethyl)cyclohexyl]amino-4,6-dideoxy-α-D-glucopyranoside,
(21) Methyl 4-[(1S,2S)-(2,4,5(OH)/3,5)-2,3,4,5-tetrahydroxy-5-(hydroxymethyl)cyclohexyl]amino-4-deoxy-α-D-glucopyranoside,
(22) [(1S,2S)-(2,4,5(OH)/3,5)-2,3,4,5-tetrahydroxy-5-(hydroxymethyl)cyclohexyl][(1R,2S)-(2,6/3,4)-4-amino-2,3-dihydroxy-6-(hydroxymethyl)cyclohexyl]amine,
(23) N-[(1R,2S)-(2,4/3,5)-2,3,4-trihydroxy-5-(hydroxymethyl)cyclohexyl]valiolamine,
(24) N-[(1R,2S)-(2,6/3,4)-4-amino-2,3-dihydroxy-6-methylcyclohexyl]valiolamine,
(25) N-[(1R,2S)-(2,6/3,4)-2,3,4-trihydroxy-6-methylcyclohexyl]valiolamine,
(26) N-[(1R,2S)-(2,4,6/3)-2,3,4-trihydroxy-6-methylcyclohexyl]valiolamine,
(27) 4-O-α-[4-[((1S)-(1,2,4,5(OH)/3,5)-2,3,4,5-tetrahydroxy-5-(hydroxymethyl)cyclohexyl)amino]-4,6-dideoxy-D-glucopyranosyl]-D-glucopyranose, and
(28) 1,6-anhydro-4-O-α-[4-[((1S)-(1,2,4,5(OH)/3,5)-2,3,4,5-tetrahydroxy-5-C-(hydroxymethyl)cyclohexyl)amino]-4,6-dideoxy-D-glucopyranosyl]-β-D-glucopyranose

Inter alia, N-(1,3-dihydroxy-2-propyl)valiolamine, namely, [2-hydroxy-1-(hydroxymethyl)ethyl]valiolamine or 1L(1S)-(1(OH),2,4,5/1,3)-5-[[2-hydroxy-1-(hydroxymethyl)-ethyl]amino]-1-C-(hydroxymethyl)-1,2,3,4-cyclohexane tetrol (general name: voglibose) is particularly preferred.

The α-glucosidase inhibitor preferably used in the present invention also includes
an N-substituted valienamine derivative represented by the general formula (II):

(wherein A has the same meaning as defined above), which is described in, for example, JP 57-64648 A, and
an N-substituted validamine derivative represented by the general formula (III):

(wherein A has the same meaning as defined above), which is described in, for example, JP 57-114554 A. Preferred examples of the N-substituted valienamine derivative represented by the above general formula (II) include acarbose (general name) (BAYg5421, Naturwissenschaften, vol. 64, 535-537 (1977), JP 54-39474 B) (chemical name: O-4,6-dideoxy-4-[[(1S,4R,5S,6S)-4,5,6-trihydroxy-3-(hydroxymethyl)-2-cyclohexen-1-yl]amino]-α-D-glucopyranosyl-(1-→4)-O-α-D-glucopyranosyl(1→4)-D-glucopyranose).

The α-glucosidase inhibitor preferred in the present invention further include
a 3,4,5-trihydroxypiperidine represented by the general formula (IV):

(wherein $R^1$ and $R^3$ may be the same or different and independently represent a hydrogen atom, an optionally substituted linear, branched, or cyclic, saturated or unsaturated aliphatic hydrocarbon group, or an optionally substituted hydrocarbon ring, aromatic ring, or hetero ring; $R^2$ represents —H, —OH, —OR', —SH, —SR', —NH$_2$, —NHR', —N(R')(R''), NH$_2$CH$_2$—, NHR'—CH$_2$—, NR'R''—CH$_2$—, —COOH, —COOR', HO—CH$_2$—, R'CO—NHCH$_2$—, R'CO—NR''CH$_2$—, R'SO$_2$NHCH$_2$—, R'SO$_2$—NR''CH$_2$—, R'—NH—CO—NH—CH$_2$—, R'—NH—CS—NH—CH$_2$—R'—O—CO—NH—CH$_2$—, —SO$_3$H, —CN, —CONH$_2$, —CONHR', or —CONR'R'', wherein R' and R'' may be the same or different and each have the same meaning as that of $R^1$; and
when $R^3$ is —CH$_2$OH and $R^2$ is a hydrogen atom or —OH, when $R^3$ is a hydrogen atom and $R^2$ is a hydrogen atom, —OH, —SO$_3$H, —CN, or —CH$_2$—NH$_2$, or when $R^3$ is —CH$_2$—NH$_2$ and $R^2$ is —OH, $R^1$ is not a hydrogen atom (—H)),
which is described in, for example, U.S. Pat. No. 4,639,436 A.

Examples of the optionally substituted linear, branched, or cyclic, saturated or unsaturated aliphatic hydrocarbon group in $R^1$ and $R^3$ of the general formula (IV) include, an alkyl group, an alkenyl group, and an alkynyl group. $R^1$, R', and R'' may be the same or different, and preferred examples thereof include an optionally substituted alkyl group having 1 to 30 (more preferably 1 to 18, and further more preferably 1 to 10) carbon atoms, an optionally substituted alkenyl group having 2 to 18 carbon atoms, a carbon atom, and an optionally substituted monocyclic, bicyclic, or tricyclic aliphatic hydrocarbon, aromatic ring, or hetero ring. Inter alia, an optionally substituted alkyl group having 1 to 10 carbon atoms is preferred. The substituent is preferably a hydroxyl group etc. $R^3$ is preferably a hydrogen atom, —CH$_3$, —CH$_2$OH, —CH$_2$—NH$_2$, NHR'—CH$_2$—, NR'R''CH$_2$—, R'CONH—CH$_2$—, R'CO—NR''CH$_2$—, X—CH$_2$— (wherein X represents a halogen atom), R'O—CH$_2$—, R'COOCH$_2$—, R'SO$_2$O—CH$_2$—, R'SO$_2$NHCH$_2$—, R'SO$_2$—NR''CH$_2$—, R'NH—CO—NH—CH$_2$—, R'NHCS—NH—CH$_2$—, R'O—CO—NH—CH$_2$—, —CN, —COON, —COOR', —CONH$_2$, —CONHR', or —CONK'R'' (wherein R' and R'' may be the same or different, and each have the same meaning as that of $R^1$, as above).

Particularly preferred example of the 3,4,5-trihydroxypiperidine represented by the general formula (IV) is a compound in which $R^1$ is —CH$_2$—CH$_2$—OH, $R^2$ is a hydrogen atom, and $R^3$ is —CH$_2$—OH (general name: miglitol, chemical name: (−)-(2R,3R,4R,5S)-1-(2-hydroxymethyl)piperidine-3,4,5-triol).

Other examples of usable 3,4,5-trihydroxypiperidine include trestatin (J. Antibiotics, vol. 36, 1157-1175 (1983) and vol. 37, 182-186 (1984); and JP 54-163511A), adiposin (J. Antibiotics, vol. 35, 1234-1236 (1982); J. Jap. Soc. Starch Sci., vol. 26, 134-144 (1979) and vol. 27, 107-113 (1980); JP 54-106402 A; JP 54-106403 A; JP 55-64509 A; JP 56-123986 A; and JP 56-125398 A), amylostatin (Agric. Biol. Chem., vol. 46, 1941-1945 (1982); JP 50-123891 A; JP 55-71494 A; and JP 55-157595 A), oligostatin (SF-1130X) (JP 53-26398 A; JP 56-43294 A; J. Antibiotics, vol. 34, 1424-1433 (1981)), and aminosugar compounds (JP 54-92909 A). In addition, α-glucosidase inhibitors of microbial origin, including the above-mentioned compounds, are reported in a review paper by E. Truscheit et al. (Angewandte Chemie, vol. 93, 738-755 (1981)). These compounds also can be used as the α-glucosidase inhibitor of the present invention.

Other examples of the compound that can be used as the α-glucosidase inhibitor of the present invention include methyl 4-[(1S,6S)-(4,6/5)-4,5,6-trihydroxy-3-hydroxymethyl-2-cyclo hexen-1-yl]amino-4,6-dideoxy-α-D-glucopyranoside (182nd American Chemical Society (ACS) National meeting abstracts paper, MEDI 69, August, 1981 in New York; J. Antibiotics, vol. 34, 1429-1433 (1981); and JP 57-24397 A) obtainable by methanolysis of acarbose and oligostatins C, 1-deoxynojirimycin (Naturwissenschaften, vol. 66, 584-585 (1979), and N-substituted derivatives thereof, for example, BAYo1248 (J. Clin. Invest., vol. 14 (2-II), 47 (1984); and Diabetologia, vol. 27 (2), 288A, 346A, 323A (1984)).

As the α-glucosidase inhibitor of the present invention, particularly preferred is voglibose (general name), acarbose (general name), or miglitol (general name), and the most preferred is voglibose or acarbose.

Further, besides the above-mentioned compounds, substances which have an α-glucosidase inhibitory activity and are usually used for food and drink are also preferable as the α-glucosidase inhibitor of the present invention. As such a substance, at least one kind selected from, for example, malt extract, salacia, mulberry leaf extract, and tea seed extract can preferably be used.

Malt extract, which is a plant extract, inhibits α-glucosidase activity and enhances the excretion of carbohydrate out of the body. Salacia is a climbing plant which belongs to Celastraceae and grows wild in Sri Lanka. The root tea thereof is said to have been used for the purpose of dieting in India for about 5000 years, and its component salacinol is believed useful for dealing with diabetes. Tea seed (TS) extract, which is one of the tea ingredients, inhibits glucosidase activity necessary for sugar absorption in the digestive tract and thereby strongly inhibits absorption of sugar (glucose). This activity serves to reduce the energy taken from carbohydrate and balance calorie intake and calorie consumption. Preferred tea seed extract is, for example, Tea Seed Extract (trade name, made by Tanglewood).

The bacteria used in the present invention are at least one kind of bacteria selected from the group consisting of bifidobacteria, lactic acid bacteria, saccharifying bacteria, and butyric acid bacteria, and specific examples thereof include bifidobacteria, such as *Bifidobacterium bifidum, B. longum, B. breve, B. adolescentis, B. infantis, B. pseudolongum,* and *B. thermophilum;* lactic acid bacilli, such as *Lactobacillus acidophilus, L. casei, L. gasseri, L. plantarum, L. delbrueckii* subsp. *bulgaricus, L. delbrueckii* subsp. *lactis, L. fermentum, L. helveticus, L. johnsonii, L. paracasei* subsp. *paracasei, L. reuteri, L. rhamnosus, L. salivarius,* and *L. brevis;* lactic acid cocci, such as *Leuconostoc mesenteroides, Streptococcus (Enterococcus) faecalis, Streptococcus (Enterococcus) faecium, Streptococcus (Enterococcus) hirae, Streptococcus thermophilus, Lactococcus lactis, L. cremoris, Tetragenococcus halophilus, Pediococcus acidilactici, P. pentosaceus,* and *Oenococcus oeni;* saccharifying bacteria, such as *Bacillus subtilis, Bacillus mesentericus,* and *Bacillus polyformenticus;* spore forming lactic acid bacteria, such as *Bacillus coagulans;* butyric acid bacteria, such as *Bacillus toyoi, B. licheniformis,* and *Clostridium butyricum;* and other useful bacteria.

These bacterial cells are readily available from organizations, such as ATCC and IFO, or foundations, such as Japan Bifidus Foundation. Alternatively, commercial products can be used suitably.

The bacteria used in the present invention are preferably at least one kind of bacteria selected from the group consisting of bifidobacteria, lactic acid bacteria, saccharifying bacteria, and butyric acid bacteria; more preferably at least one kind of bacteria selected from the group consisting of bifidobacteria, lactic acid bacteria, and saccharifying bacteria; and furthermore preferably lactic acid bacteria and/or bifidobacteria. Inter alia, more preferred are bifidobacteria; further more preferred are *Bifidobacterium bifidum, Bifidobacterium longum, Bifidobacterium infantis,* and *Bifidobacterium breve;* and particularly preferred are *Bifidobacterium bifidum* and *Bifidobacterium longum.* In the case where two or more kinds of bacteria are used in combination, preferred combination is: bifidobacteria, lactic acid bacteria, and saccharifying bacteria; bifidobacteria and lactic acid bacteria; bifidobacteria and saccharifying bacteria; or lactic acid bacteria and saccharifying bacteria. Specifically, preferred is a combination of two or more kinds selected from (i) *Bifidobacterium bifidum,* (ii) *Lactobacillus acidophilus,* (iii) *Lactobacillus gasseri,* (iv) *Streptococcus (Enterococcus) faecalis,* (v) *Streptococcus (Enterococcus) faecium,* (vi) *Bacillus subtilis,* and (vii) *Bacillus mesentericus.* Inter alia, more preferred is a combination of two or more kinds selected from (i) *Bifidobacterium bifidum* G9-1, (ii) *Lactobacillus acidophilus* KS-13, (iii) *Lactobacillus gasseri,* (iv) *Streptococcus (Enterococcus) faecalis* 129BIO 3B, (v) *Streptococcus (Enterococcus) faecium,* (vi) *Bacillus subtilis* 129 BIO H(α), and (vii) *Bacillus mesentericus.* As the bacteria used in the present invention, more preferred are one or more kinds selected from the group consisting of *Bifidobacterium bifidum* G9-1, *Lactobacillus acidophilus* KS-13, *Streptococcus (Enterococcus)* faecalis 129 BIO 3B, and *Bacillus subtilis* 129 BIO H(α); and particularly preferred are one or more kinds selected from the group consisting of *Bifidobacterium bifidum* G9-1, *Streptococcus (Enterococcus) faecalis* 129 BIO 3B, and *Bacillus subtilis* 129 BIO H(α). In the case where two or more kinds of bifidobacteria, lactic acid bacteria, saccharifying bacteria, and butyric acid bacteria are used in combination, the blending ratio is not particularly limited.

The above-mentioned bacterial cells can be obtained by culture under publicly known conditions or similar conditions. For example, in the case of bifidobacteria or lactic acid bacteria, usually one or more kinds of the bifidobacteria or lactic acid bacteria are cultured in a liquid culture medium containing glucose, yeast extract, peptone, etc. aerobically or anaerobically at about 25 to 45° C. for about 4 to 72 hours. By cell collection from the culture fluid and subsequent washing, wet bacterial cells are obtained. In the case of saccharifying bacteria, usually one or more kinds of the bacteria are cultured in an agar culture medium containing meat extract, peptone from casein, sodium chloride, etc. aerobically at about 25 to 45° C. for about 4 to 72 hours. By cell collection from the culture medium and subsequent washing, wet bacterial cells are obtained.

The at least one kind of bacteria selected from the group consisting of bifidobacteria, lactic acid bacteria, saccharifying bacteria, and butyric acid bacteria for use in the present invention are preferably viable bacteria, but treated bacterial cells can also be used. The "treated bacterial cells" means at least one kind of bacteria selected from the group consisting of bifidobacteria, lactic acid bacteria, saccharifying bacteria, and butyric acid bacteria treated in some way, and the treatment is not particularly limited. Specific examples of the treated bacterial cells include cell lysates obtained by ultrasound etc., culture fluids or culture supernatants, and solid residues thereof obtained by solid-liquid separation means, such as filtration and centrifugation. The examples also include treated fluids from which cell wall has been removed by enzymatic or mechanical means, and protein complexes (proteins, lipoproteins, glycoproteins, etc.) or peptide complexes (peptides, glycopeptides, etc.) obtainable by treatment with trichloroacetic acid or by salting-out. Further, concentrates, dilutions, and dried matters thereof are also included in the treated bacterial cells. In addition, the treated bacterial cells of the present invention also include ones obtainable by further treatment of the above-mentioned cell lysates, culture fluids or culture supernatants by, for example, various types of chromatography. Killed bacterial cells of the at least one kind of bacteria selected from the group consisting of bifidobacteria, lactic acid bacteria, saccharifying bacteria, and butyric acid bacteria are also included in the treated bacterial cells of the present invention. The killed bacterial cells can be obtained by, for example, enzymatic treatment, heat treatment at about 100° C., treatment with drugs, such as antibiotics, treatment with chemicals, such as formalin, treatment with radiation, such as γ ray, etc.

The bacteria used in the present invention may be a dried product (dried bacterial cell product), and preferably single micron-sized dried bacterial cell product. The dried bacterial cell product usually means individual dried bacterial cells or an aggregate of dried bacterial cells. The "single micron" means a size of 1 to 10 μm by rounding to the nearest whole number. When a single micron-sized dried bacterial cell product is used as the at least one kind of bacteria selected from the group consisting of bifidobacteria, lactic acid bacteria, saccharifying bacteria, and butyric acid bacteria used for the present invention, the viable cell ratio in the preparation is increased. As a result, the hypoglycemic activity is enhanced, and the effect to prevent and improve lifestyle-related diseases, such as diabetes and obesity, is also enhanced.

Hereinafter, a preferable preparation method of a dried bacterial cell product will be described. The above-mentioned bacterial cells are dispersed in a solvent to prepare a bacterial cell fluid. The solvent may be any solvent known in the art, but preferred is water. Ethanol may be added if desired. In the case ethanol is added, since ethanol vaporizes first and then water vaporizes, stepwise drying is possible. The bacterial cell fluid may be a suspension. The solvent may be the same as shown above. In preparation of the suspension, a suspending agent, for example, sodium alginate etc. may be used.

To the bacterial cell fluid, additives generally used in the art, such as a protective agent, an excipient, a binder, a disintegrant, or an antistat, may be added in a usual blending ratio.

The above-mentioned bacterial cell fluid is subjected to drying procedure using a spray dryer for preparation of a dried bacterial cell product. Preferably used is a spray dryer equipped with an atomizer capable of forming single micron-sized sprayed droplets. Sprayed droplets having a very small particle diameter have a large surface area per unit mass, and therefore efficiently contact with hot drying air, resulting in improved productivity.

The "single micron-sized sprayed droplets" means sprayed droplets having a particle diameter of 1 to 10 μm by rounding to the nearest whole number.

Examples of the spray dryer include a spray dryer of which the atomizer is, for example, a rotary atomizer (rotary disk), a pressure nozzle, or a 2-fluid nozzle or a 4-fluid nozzle utilizing the force of a compressed gas.

The spray dryer may be of any type of the above-mentioned spray dryers as long as single micron-sized sprayed droplets can be formed, but preferred is a spray dryer having a 4-fluid nozzle.

As for the structure of the 4-fluid nozzle of a spray dryer having a 4-fluid nozzle, two systems each comprising a gas channel and a liquid channel are symmetrically arranged in a nozzle edge, which has a slanting inner surface along which fluids flow.

Preferred is a spray dryer of the external mixing type, where a compressed gas and a liquid are focused from both sides on the collision focal spot at the tip of the nozzle edge. This type enables prolonged spraying without nozzle clogging.

Figure 4:
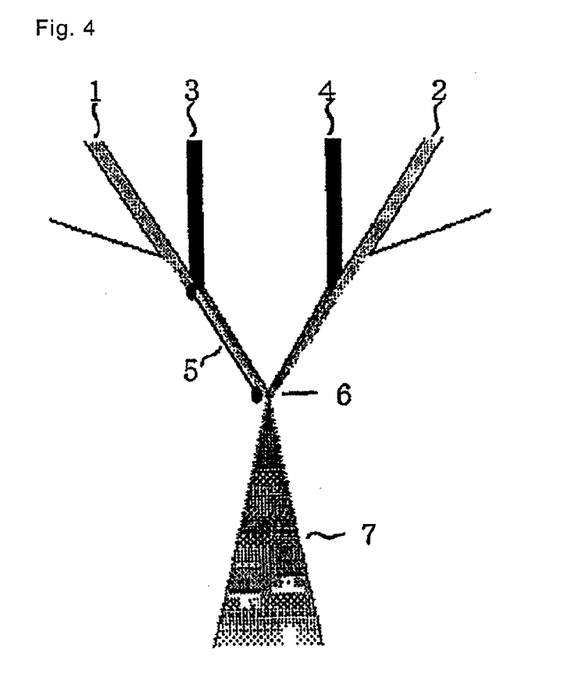
FIG. 4 shows the internal structure of the nozzle edge of a spray dryer with a 4-channel nozzle.

The spray dryer having a 4-channel nozzle will be described in more detail referring to FIG. 4. In the nozzle edge of the 4-channel nozzle, the bacterial cell fluid coming out of the liquid channel 3 or 4 is thinly extended along the fluid flow surface 5 by a high-speed gas flow coming out of the gas channel 1 or 2 and then atomized by shock wave generated at the collision focal spot 6 at the tip of the nozzle edge, forming single micron-sized sprayed droplets 7.

As the compressed gas, air, carbon dioxide gas, inert gases, such as nitrogen gas or argon gas, etc. can be used, for example. In particular, in cases of spray drying of a substance susceptible to oxidization, preferably used is carbon dioxide gas or an inert gas, such as nitrogen gas or argon gas.

The pressure of the compressed gas is usually about 1 to 15 kgw/cm$^2$, and preferably about 3 to 8 kgw/cm$^2$.

The flow volume of the gas in a nozzle per 1 mm of the nozzle edge is usually about 1 to 100 L/min, and preferably about 10 to 20 L/min.

In normal cases, subsequently, the sprayed droplets are brought into contact with hot drying air in a drying chamber, where water is vaporized and thereby a dried bacterial cell product is obtained.

The inlet temperature of the drying chamber is usually about 2 to 400° C., preferably about 5 to 250° C., and more preferably about 5 to 150° C. Even when the inlet temperature is as high as about 200 to 400° C., the temperature in the drying chamber does not become that high due to heat absorption by water vaporization. By shortening the residence time in the drying chamber, death of or damage to viable cells can be suppressed to some extent.

The outlet temperature is usually about 0 to 120° C., preferably about 5 to 90° C., and more preferably about 5 to 70° C.

In a spray dryer having a 4-channel nozzle, where two liquid channels exist, two different kinds of bacterial cell fluids, or a bacterial cell fluid and another solution or suspension can be simultaneously sprayed to give a dried bacterial cell product as a mixture thereof.

For example, by simultaneously spraying two different kinds of bacterial cell fluids, a dried bacterial cell product containing the two kinds of bacterial cells can be obtained.

As described above, a dried bacterial cell product having a very small particle diameter has an advantage that the viable cell ratio is increased and therefore a preparation having a higher viable cell ratio can be provided.

That is, in order to obtain a single micron-sized dried bacterial cell product, preferred is spraying single micron-sized droplets. Sprayed droplets having a smaller particle diameter have a larger surface area per unit mass, and therefore efficiently contact with hot drying air. Therefore, death of or damage to viable cells caused by the heat of the hot drying air can be minimized. As a result, the viable cell ratio is increased and a dried bacterial cell product having many viable cells can be obtained.

The combination of the at least one kind of bacteria selected from the group consisting of bifidobacteria, lactic acid bacteria, saccharifying bacteria, and butyric acid bacteria, with an α-glucosidase inhibitor is not particularly limited in the present invention. When the α-glucosidase inhibitor is a compound represented by the above general formula (I), preferably voglibose (general name), preferably used is at least one kind selected from the group consisting of bifidobacteria, lactic acid bacteria, and saccharifying bacteria. Inter alia, particularly preferred is use of bifidobacteria, and also preferred is use of lactic acid bacteria and/or saccharifying bacteria, with bifidobacteria. When the α-glucosidase inhibitor is a compound represented by the above general formula (II), preferably acarbose (general name), preferably used is at least one kind selected from the group consisting of lactic acid bacteria, saccharifying bacteria, and bifidobacteria. Inter alia, more preferred is use of lactic acid bacteria and/or saccharifying bacteria, and particularly preferred are lactic acid bacteria and saccharifying bacteria. Bifidobacteria may be used with lactic acid bacteria and saccharifying bacteria. The use of an α-glucosidase inhibitor and bacteria in such a combination can significantly enhance the hypoglycemic activity of the α-glucosidase inhibitor and/or the bacteria.

Preferred embodiments of the present invention include a bifidobacteria-containing hypoglycemic effect enhancer for enhancing the activity of voglibose, a lactic acid bacteria-containing hypoglycemic effect enhancer for enhancing the activity of acarbose, a voglibose-containing hypoglycemic effect enhancer for enhancing the activity of bifidobacteria, and an acarbose-containing hypoglycemic effect enhancer for enhancing the activity of lactic acid bacteria.

The hypoglycemic effect enhancer of the present invention 1 is readily prepared by mixing at least one kind of bacteria selected from the group consisting of bifidobacteria, lactic acid bacteria, saccharifying bacteria, and butyric acid bacteria, and other ingredients. The hypoglycemic effect enhancer of the present invention 2 is readily prepared by mixing the above-mentioned α-glucosidase inhibitor and other ingredients. Other ingredients are not particularly limited as long as the effect of the present invention is exerted. The hypoglycemic effect enhancer of the present invention can be used in the form of a drug, a quasi-drug, a food or drink, a diet, or the like. Such a drug containing the hypoglycemic effect enhancer of the present invention is also included in the present invention.

In the present invention, the method of administering an α-glucosidase inhibitor in combination with at least one kind of bacteria selected from the group consisting of bifidobacteria, lactic acid bacteria, saccharifying bacteria, and butyric acid bacteria is not particularly limited as long as the effect of the present invention is exerted. Examples of the method include a method in which a preparation (composition) containing an α-glucosidase inhibitor and a preparation (composition) containing at least one kind of bacteria selected from the group consisting of bifidobacteria, lactic acid bacteria, saccharifying bacteria, and butyric acid bacteria are separately prepared and administered at the same time or at different times; and a method in which a preparation (composition) containing both an α-glucosidase inhibitor and at least one kind of bacteria selected from the group consisting of bifidobacteria, lactic acid bacteria, saccharifying bacteria, and butyric acid bacteria is administered. Preferred is the method in which a preparation containing both the ingredients is prepared and administered.

The dosage form of the preparation containing an α-glucosidase inhibitor alone, of the preparation containing at least one kind of bacteria selected from the group consisting of bifidobacteria, lactic acid bacteria, saccharifying bacteria, and butyric acid bacteria alone, and of the preparation containing the both should be decided in consideration of the physicochemical properties, biological properties, etc. of each ingredient so that the form is suitable for administration. As drugs, preferred are internal drugs suitable for oral administration. Examples of the dosage form of the internal drugs include a tablet, a pellet, a fine granule, a powder, a granule, a pill, a chewable tablet, a troche, a solution, and a suspension. Inter alia, a tablet or a powder is preferred. Further, each preparation may appropriately contain, besides an α-glucosidase inhibitor and/or at least one kind of bacteria selected from the group consisting of bifidobacteria, lactic acid bacteria, saccharifying bacteria, and butyric acid bacteria, publicly known additives used in the art, such as an excipient (for example, lactose, starch, crystalline cellulose, sodium phosphate, or the like), a binder (for example, starch, gelatin, carmellose sodium, methylcellulose, hydroxypropylmethylcellulose, hydroxypropylcellulose, polyvinyl pyrrolidone, or the like), a disintegrant (for example, starch, carmellose sodium, or the like), a lubricant (for example, talc, magnesium stearate, calcium stearate, macrogol, sucrose fatty acid ester, or the like), a stabilizer (sodium hydrogensulfite, sodium thiosulfate, sodium edetate, sodium citrate, ascorbic acid, dibutyl hydroxytoluene, or the like), a colorant, a flavor, a brightener, etc. The amount of the at least one kind of bacteria selected from the group consisting of bifidobacteria, lactic acid bacteria, saccharifying bacteria, and butyric acid bacteria in the final preparation usually can be determined by selecting an appropriate amount from the range of about 0.000001 to 99% by mass. The amount of the α-glucosidase inhibitor in the final preparation usually can be determined by selecting an appropriate amount from the range of about 0.0001 to 99% by mass.

The composition containing an α-glucosidase inhibitor and at least one kind of bacteria selected from the group consisting of bifidobacteria, lactic acid bacteria, saccharifying bacteria, and butyric acid bacteria can be prepared by mixing the ingredients according to a conventional preparation method, and the blending ratio of the α-glucosidase inhibitor and the at least one kind of bacteria selected from the group consisting of bifidobacteria, lactic acid bacteria, saccharifying bacteria, and butyric acid bacteria is preferably about $10^3$ to $10^{12}$ cells of the bacteria relative to about 0.05 to 500 mg of the α-glucosidase inhibitor, and particularly preferably about $10^5$ to $10^{11}$ cells of the bacteria relative to about 0.01 to 300 mg of the α-glucosidase inhibitor.

The at least one kind of bacteria selected from the group consisting of bifidobacteria, lactic acid bacteria, saccharifying bacteria, and butyric acid bacteria are generally anaerobic and have a low tolerance for air or oxygen under dry conditions and for high temperature and moisture. Therefore, the formulation of such a composition is preferably performed in the presence of an inert gas or in vacuo at a low temperature.

The composition containing an α-glucosidase inhibitor and at least one kind of bacteria selected from the group consisting of bifidobacteria, lactic acid bacteria, saccharifying bacteria, and butyric may be prepared as a solid preparation either by a dry method where powders are simply mixed or compressed into a granule or a tablet, or by a wet method where, with use of a solution of a binder, kneading and drying are performed to give an objective solid preparation, such as a granule or a tablet. Further, a powder or a granule obtained as above may be encapsulated to give a capsule.

For example, to prepare a tablet, a publicly known tableting machine is preferably used. Examples of the tableting machine include a single punch tableting machine and a rotary tableting machine. Also, a pill, a chewable tablet, or a troche may be prepared according to a publicly known method, for example, by the same means as that for tablet preparation.

In order to obtain a uniform mixture by mixing a slight amount of an active ingredient (an α-glucosidase inhibitor and/or at least one kind of bacteria selected from the group consisting of bifidobacteria, lactic acid bacteria, saccharifying bacteria, and butyric acid bacteria) with a large amount of another powder, the so-called gradual mixing method is preferably employed. For example, by well mixing the active ingredient with 100 to 200 times its volume of another powder and subsequently mixing the obtained uniform powder mixture with the remaining powder, a uniform powder mixture can be obtained.

To dry an aqueous substance, L-drying, freeze-drying, spray drying, or other means can be used. To obtain dried bacterial cells of at least one kind of bacteria selected from the group consisting of bifidobacteria, lactic acid bacteria, saccharifying bacteria, and butyric acid bacteria, it is practicable to suspend the bacteria in a neutral buffer solution supplemented with an appropriate stabilizer such as monosodium glutamate, adonitol, or the like and then dry the suspension by a publicly known method.

In the present invention, the dosage amount of the α-glucosidase inhibitor for an adult is usually about 0.001 to 500 mg/time, preferably about 0.001 to 100 mg/time, more preferably about 0.002 to 100 mg/time, and this amount is preferably administered orally twice to 4 times a day within 1 hour before to 2 hours after meals. In particular, when the α-glucosidase inhibitor is a valiolamine derivative represented by the general formula (I), it is effective that about 0.001 to 20 mg/time (more preferably about 0.002 to 20 mg/time) of the compound is orally administered to an adult twice to 4 times a day, preferably at a suitable time within 1 hour before to 2 hours after meals.

When viable cells are used in the present invention, the effective dosage amount of the at least one kind of bacteria selected from the group consisting of bifidobacteria, lactic acid bacteria, saccharifying bacteria, and butyric acid bacteria for an adult is, in terms of viable cells, usually about $10^3$ to $10^{12}$ cells/time, preferably about $10^5$ to $10^{10}$ cells/time, more preferably about $10^6$ to $10^{10}$ cells/time, and this amount is orally administered twice to 4 times a day, preferably within about 1 hour before to about 2 hours after meals. Here, the method for measuring the viable cell count in the preparation varies depending on the bacterial cells, but such measurement can be readily performed according to, for example, the quantitative determination method for the corresponding bacteria described in the Japanese Pharmaceutical Codex.

The hypoglycemic effect enhancer of the present invention can be preferably applied to individuals (animals) with lifestyle-related diseases, such as diabetes, hypertension, hyperlipidemia, cardiovascular disease, and cardiac disease or individuals with potential risks thereof. Individuals with obesity or potential obesity in need of weight loss are also preferred subjects. Further, individuals with obesity and complicating diabetes, hyperlipidemia, etc. (metabolic syndrome) or individuals with potential risks thereof are more preferred. Inter alia, individuals with obesity and/or complicating diabetes or individuals with potential risks thereof are more preferred, individuals with obesity and/or complicating diabetes are further more preferred, and individuals with diabetes are in particular preferred. A preferred individual is a mammal, such as a human, a mouse, a rat, a rabbit, a dog, a cat, a cow, a horse, a pig, and an ape, and particularly preferred is a human.

The hypoglycemic effect enhancer of the present invention even in a less amount, due to concomitant use of an α-glucosidase inhibitor and at least one kind of bacteria selected from the group consisting of bifidobacteria, lactic acid bacteria, saccharifying bacteria, and butyric acid bacteria, synergistically enhances the hypoglycemic activity of the α-glucosidase inhibitor and/or the bacteria, and therefore is effective in prevention or treatment of diabetes or obesity, easy to administer, and almost free from side effects.

The hypoglycemic effect enhancers of the present invention 1 and 2 can be used not only as the above-mentioned drugs but also as a food or drink product such as a functional food, a food for specified health use, or a drinkable preparation. A food or drink composition for enhancing the hypoglycemic activity of an α-glucosidase inhibitor, the composition comprising the hypoglycemic effect enhancer of the present invention 1, is also included in the present invention. A food or drink composition for enhancing the hypoglycemic activity of lactic acid bacteria, the composition comprising the hypoglycemic effect enhancer of the present invention 2, is also included in the present invention. Feeding the food or drink composition of the present invention to a mammal including a human with lifestyle-related diseases, such as diabetes and obesity, or with potential risks thereof can prevent or improve the lifestyle-related diseases. The amount of the at least one kind of bacteria selected from the group consisting of bifidobacteria, lactic acid bacteria, saccharifying bacteria, and butyric acid bacteria in the final food or drink composition usually can be determined by selecting an appropriate amount from the range of about 0.000001 to 99% by mass. The amount of the α-glucosidase inhibitor in the final food or drink composition usually can be determined by selecting an appropriate amount from the range of about 0.0001 to 99% by mass.

In the present invention, the method of feeding an α-glucosidase inhibitor in combination with at least one kind of bacteria selected from the group consisting of bifidobacteria, lactic acid bacteria, saccharifying bacteria, and butyric acid bacteria is not particularly limited as long as the effect of the present invention is exerted. Examples of the method include a method in which a composition containing an α-glucosidase inhibitor and a composition containing at least one kind of bacteria selected from the group consisting of bifidobacteria, lactic acid bacteria, saccharifying bacteria, and butyric acid bacteria are separately prepared and fed at the same time or at different times; and a method in which a composition containing both an α-glucosidase inhibitor and at least one kind of bacteria selected from the group consisting of bifidobacteria, lactic acid bacteria, saccharifying bacteria, and butyric acid bacteria is fed. Preferred is the method in which a composition containing both the ingredients is prepared and fed.

In the case where the hypoglycemic effect enhancer of the present invention is used as a food or drink composition, the form is not particularly limited. The food or drink composition may also be in a processed form, such as a natural liquid diet, a low residue diet, an elemental diet, or a drinkable preparation. The food or drink composition of the present invention may also be a readily-soluble preparation to be added to an alcoholic beverage or mineral water at the time of use. More specifically, the food or drink composition of the present invention may be in the form of, for example, confectionery, such as a biscuit, a cookie, a cake, a candy, chocolate, chewing gum, and a Japanese-style confection; bread, noodles, rice, or processed products thereof; fermented foods, such as sake and a medicinal drink; animal products, such as yogurt, ham, bacon, sausage, and mayonnaise; drinks, such as a fruit drink, a soft drink, a sports drink, an alcoholic drink, and a tea drink; etc.

The food or drink composition of the present invention may be fed to a patient, for example, in the form of a food prepared on the spot under the supervision of a nutritionist, based on a dietary recipe prescribed by a doctor, by addition of the food or drink composition of the present invention to any food in the process of hospital food preparation. The food or drink composition of the present invention may be in a liquid form or in a solid form such as a powder and a granule.

The food or drink composition of the present invention may contain an auxiliary ingredient commonly used in the food field. Examples of the auxiliary ingredient include lactose, sucrose, liquid sugar, honey, magnesium stearate, oxypropylcellulose, various vitamins, a trace element, citric acid, malic acid, a flavor, a mineral salt, etc.

The amount of the food or drink composition of the present invention to be fed to a mammal varies depending on the lifestyle-related disease conditions, age, sex, etc. of the mammal, but it is preferred that the α-glucosidase inhibitor and the at least one kind of bacteria selected from the group consisting of bifidobacteria, lactic acid bacteria, saccharifying bacteria, and butyric acid bacteria are each fed in a similar amount to that in the case of drugs described above.

The present invention also includes use of lactic acid bacteria for enhancing the hypoglycemic activity of an α-glucosidase inhibitor. The present invention further includes use of an α-glucosidase inhibitor for enhancing the hypoglycemic activity of at least one kind of bacteria selected from the group consisting of bifidobacteria, lactic acid bacteria, saccharifying bacteria, and butyric acid bacteria. The α-glucosidase inhibitor, the at least one kind of bacteria selected from the group consisting of bifidobacteria, lactic acid bacteria, saccharifying bacteria, and butyric acid bacteria, used in the present invention, the preferred embodiments thereof, etc. are similar to those of the hypoglycemic effect enhancer described above.

The present invention also includes an expression promoter for the hypoglycemic activity of an α-glucosidase inhibitor, the promoter comprising at least one kind of bacteria selected from the group consisting of bifidobacteria, lactic acid bacteria, saccharifying bacteria, and butyric acid bacteria. Concomitant use of an α-glucosidase inhibitor and at least one kind of bacteria selected from the group consisting of bifidobacteria, lactic acid bacteria, saccharifying bacteria, and butyric acid bacteria exerts an effective hypoglycemic effect in a shorter period even when the amount of the α-glucosidase inhibitor is less than that in the case where the inhibitor is administered alone for the hypoglycemic effect. Therefore, concomitant use of the above bacteria and an α-glucosidase inhibitor can effectively exert the hypoglycemic activity of the inhibitor in a shorter period even when the amount of the α-glucosidase inhibitor is reduced.

In concomitant use of an α-glucosidase inhibitor and at least one kind of bacteria selected from the group consisting of bifidobacteria, lactic acid bacteria, saccharifying bacteria, and butyric acid bacteria, for example, when about 0.2 to 100 mg/time of the α-glucosidase inhibitor is orally administered twice to 4 times a day before meals, effective activity of improving glucose tolerance is obtainable about 4 to 8 weeks after the start of the administration. The preferred amount of the at least one kind of bacteria selected from the group consisting of bifidobacteria, lactic acid bacteria, saccharifying bacteria, and butyric acid bacteria used in the present invention is the same as that of the hypoglycemic effect enhancer described above. The expression promoter for the hypoglycemic activity of an α-glucosidase inhibitor of the present invention and the preferred embodiments thereof are the same as described regarding the hypoglycemic effect enhancer for enhancing the activity of an α-glucosidase inhibitor described above.

The present invention also includes a method for enhancing the hypoglycemic activity of an α-glucosidase inhibitor, the method comprising administering to an animal at least one kind of bacteria selected from the group consisting of bifidobacteria, lactic acid bacteria, saccharifying bacteria, and butyric acid bacteria in combination with an α-glucosidase inhibitor.

The present invention also includes a method for enhancing the hypoglycemic activity of at least one kind of bacteria selected from the group consisting of bifidobacteria, lactic acid bacteria, saccharifying bacteria, and butyric acid bacteria, the method comprising administering to an animal an α-glucosidase inhibitor in combination with the bacteria.

The present invention further includes a method for promoting the expression of the hypoglycemic activity of an α-glucosidase inhibitor, the method comprising administering to an animal at least one kind of bacteria selected from the group consisting of bifidobacteria, lactic acid bacteria, saccharifying bacteria, and butyric acid bacteria in combination with an α-glucosidase inhibitor.

Preferred examples of the animal in the present invention include, as described above, an individual (animal) with lifestyle-related diseases, such as diabetes, hypertension, hyperlipidemia, cardiovascular disease, and cardiac disease or an individual with potential risks thereof; an individual with obesity or potential obesity in need of weight loss; and an individual with obesity and complicating diabetes, hyperlipidemia, etc. (metabolic syndrome) or an individual with potential risks thereof. The administration method and the amounts of the at least one kind of bacteria selected from the group consisting of bifidobacteria, lactic acid bacteria, saccharifying bacteria, and butyric acid bacteria, and the α-glucosidase inhibitor used in the present invention are the same as those of the hypoglycemic effect enhancer described above.

EXAMPLES

Hereinafter, the present invention will be illustrated in more detail by Examples, but it is not limited thereto. As used in the Examples, % expresses % by mass unless otherwise stated.

Example 1

Preparation of a Dried Product of *Bifidobacterial* Cells, and Measurement of the Viable Cell Count in the Dried Bacterial Cell Product 1. Preparation Method of Bacteria (BBG9-1: *Bifidobacterium bifidum* G9-1

Preparation of a dried product of bacterial cells BBG9-1 was performed as follows. A cryopreserved strain of BBG9-1 (preserved by Biofermin Pharmaceutical Co., Ltd.) was statically cultured at 37° C. for 24 hours. Then, into 100 parts of liquid medium (1) for the test of bifidobacteria (described in the section "Bifidobacteria" of the Japanese Pharmaceutical Codex), 1 part (volume ratio) of the cultured bacterial cell fluid was inoculated and statically cultured at 37° C. for 18 hours. The obtained culture fluid was centrifuged and bacterial cells were washed with water 3 times. To this, an appropriate amount of water was added. Then, to 1 kg of the wet bacterial cells, 0.1 kg of glutamate and 0.5 kg of dextrin were added. With use of a spray dryer, a dried product of the bacterial cells was obtained. The bifidobacterial strain BBG9-1 is an ingredient contained in an ethical drug, Biofermin tablets (trade name, made by Biofermin Pharmaceutical Co., Ltd.) etc., and therefore is available from the tablets or the like by a conventional purification method.

The above-mentioned liquid medium (1) for the test of bifidobacteria was prepared according to the method described in the section "Bifidobacteria" of the Japanese Pharmaceutical Codex. That is, the following ingredients were mixed and sterilized by heat at 121° C. for 10 minutes with use of a high-pressure steam sterilizer.

| | |
|---|---|
| Beef-liver extract | 1000 mL |
| Peptone from casein | 10 g |
| Glucose | 10 g |
| Polysorbate 80 | 1 g |
| L-cystine (Dissolved in 2 mL of dilute hydrochloric acid before addition.) | 0.5 g |
| pH | 7.0 to 7.2 |

2. Measurement of Viable Cell Count in the Dried Bacterial Cell Product

The viable cell count was measured according to the quantitative determination method for bifidobacteria described in the section "Bifidobacteria" of the Japanese Pharmaceutical Codex. That is, precisely weighed 5 g of the dried bacterial cell product was added to 30 mL of the diluent (2), and the mixture was shaken vigorously. The diluent (2) was further added until the total volume reached exactly 50 mL, and then the mixture was shaken well again. 10-fold dilution, where precisely measured 1 mL of the bacterial cell fluid was added to precisely dispensed 9 mL of the diluent (2), was repeated so that the viable cell count was reduced to 20 to 200 cells/mL. Into a Petri dish on which 1 mL of the diluted fluid was placed, 20 mL of the agar medium for the test of bifidobacteria kept at 50° C. was added, and quickly mixed for solidification. After anaerobic culture at 37° C. for 48 to 72 hours, the colonies appeared were counted. The viable cell count in the dried bacterial cell product was calculated based on the colony count and the dilution ratio. The viable cell count in the dried bacterial cell product obtained in above 1. was $3.4 \times 10^{11}$ CFU/g.

The preparation method of the diluent (2) used in the Examples is shown below.

Preparation Method of the Diluent (2)

The diluent (2) was prepared according to the method described in the section "Bifidobacteria" of the Japanese Pharmaceutical Codex. That is, the following ingredients were mixed and sterilized by heat at 121° C. for 15 minutes with use of a high-pressure steam sterilizer.

| | |
|---|---|
| Disodium hydrogen phosphate, anhydrous | 6.0 g |
| Potassium dihydrogen phosphate | 4.5 g |
| Polysorbate 80 | 0.5 g |
| L-cysteine hydrochloride | 0.5 g |
| Agar | 1.0 g |
| Purified water | 1000 mL |
| pH | 6.8 to 7.0 |

The preparation method of the agar medium for the test of bifidobacteria used in this Example is shown below.

According to the method described in the section "Bifidobacteria" of the Japanese Pharmaceutical Codex, the following ingredients were mixed and sterilized by heat at 121° C. for 15 minutes with use of a high-pressure steam sterilizer and used.

| | |
|---|---|
| Porcine liver extract | 1000 mL |
| Peptone from casein | 20 g |
| Lactose | 20 g |
| Glucose | 10 g |
| Sodium chloride | 5 g |
| Potassium dihydrogenphosphate | 4 g |
| Monosodium L-glutamate | 2 g |
| L-cystine (Dissolved in 10% sodium hydroxide solution before addition.) | 2 g |
| Agar | 15 g |
| pH | 6.7 to 6.9 |

Example 2

Hypoglycemic Activity Enhancement by Concomitant Use of Bifidobacteria and an α-Glucosidase Inhibitor The BBG9-1 obtained by the method of Example 1 was used as lactic acid bacteria and voglibose was used as the α-glucosidase inhibitor. As the voglibose, BASEN (registered trade name) tablets 0.2 (made by Takeda Pharmaceutical Company Ltd.) were crushed and used.

Female KK-$A^y$ mice (strain name KK-$A^y$/TaJcl) at 8 weeks old were purchased (from CLEA Japan, Inc.) and preliminarily reared in separate cages for 2 weeks. A KK-$A^y$ mouse is a diabetic model mouse. In the preliminary rearing, free access to a commercial powder diet (trade name: CE-2, made by CLEA Japan, Inc.) and tap water was provided. On the first day of the experiment, the oral glucose tolerance test (OGTT) was conducted. That is, to the mice kept fasted from the previous day, a glucose solution ((2 g in 5 mL)/kg) was orally administered. Before and 15, 30, 60, and 120 minutes after the administration, the blood was made to leak from a caudal vein, and the glucose concentration in the blood was measured with use of a commercial blood glucose meter for self-check (trade name: Accu-Check Aviva, made by Roche Diagnostics). The area under the blood concentration-time curve (AUC) was calculated, and based on the AUC, the mice were divided into the following 4 groups A to D (8 mice/group). The grouped mice were given free access to the test diet.

Group A: a group fed with CE-2 containing 10% dextrin.
Group B: a group fed with CE-2 containing 10% BBG9-1 dried bacterial cells ($3.4 \times 10^{11}$/g) obtained by the method of Example 1.
Group C: a group fed with CE-2 containing 10% dextrin and 0.0003% voglibose.
Group D: a group fed with CE-2 containing 10% BBG9-1 dried bacterial cells ($3.4 \times 10^{11}$/g) obtained by the method of Example 1 and 0.0003% voglibose.

Each group was fed with the test diet for 2 weeks as above, fasted overnight, and then measured for fasting glucose level with use of Accu-Check Aviva. After the test diet was fed for additional 4 weeks (6 weeks in total), OGTT was conducted for evaluation of glucose tolerance improving activity. The significant difference of each group from Group A was evaluated using Durmett's test, and the significant difference between 2 groups was evaluated using t-test.

(Results)

Figure 1:
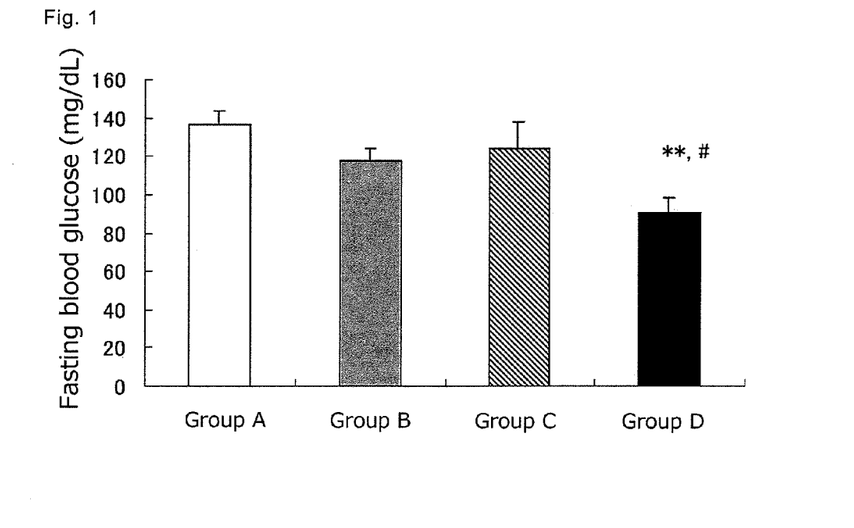
FIG. 1 shows the inhibitory effect of the hypoglycemic effect enhancer of the present invention against increase in the blood glucose level of diabetic model mice in the fasting state.
Figure 2:
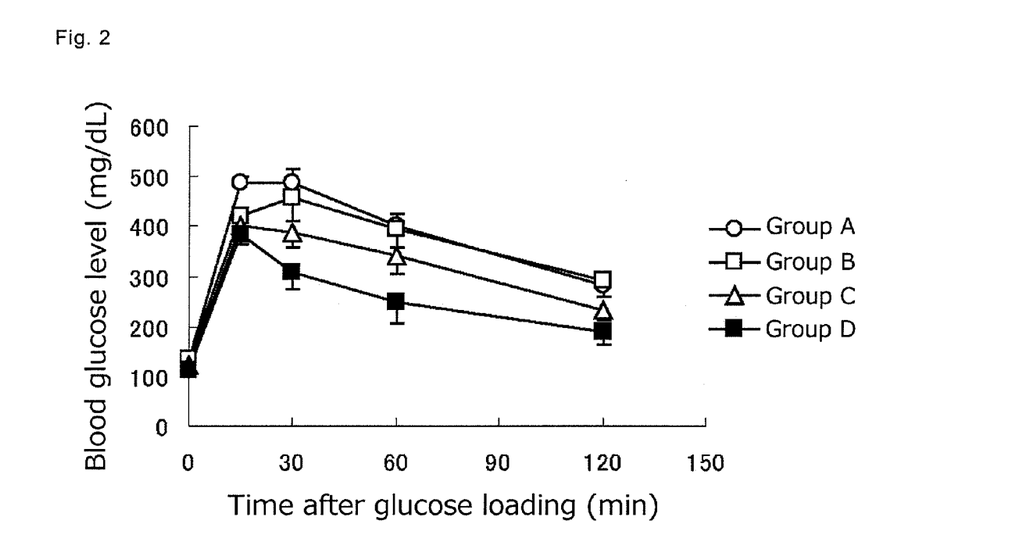
FIG. 2 shows the inhibitory effect of the hypoglycemic effect enhancer of the present invention against increase in the blood glucose level of diabetic model mice after glucose loading.
Figure 3:
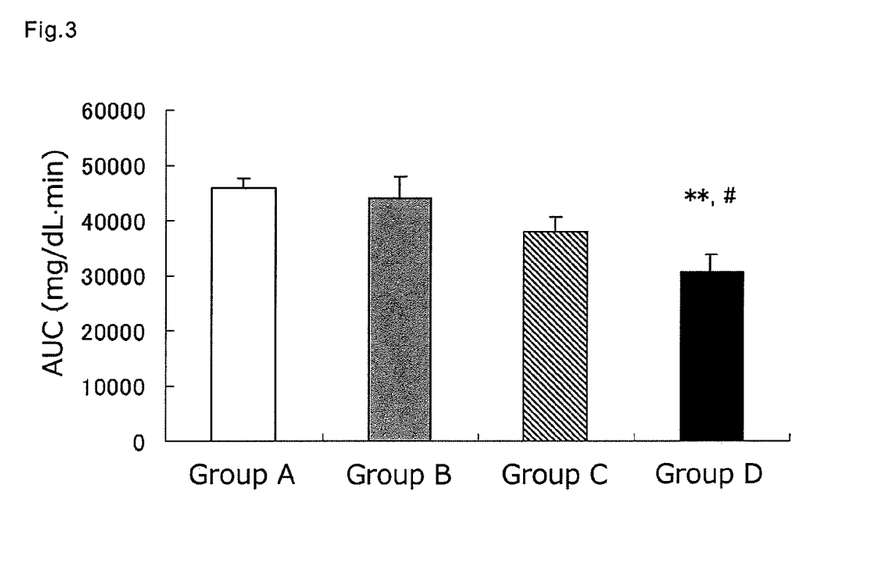
FIG. 3 shows the inhibitory effect of the hypoglycemic effect enhancer of the present invention against increase in the blood glucose level of diabetic model mice after glucose loading, using the area under the blood concentration-time curve (AUC) as an indicator.

FIG. 1 shows the fasting blood glucose levels of the Group A to D mice after 2-week feeding of the test diet. FIG. 2 shows the blood glucose levels in the OGTT after 6-week feeding, and FIG. 3 shows the AUC in the same conditions. As FIG. 1 clearly shows, while neither BBG9-1 alone nor voglibose alone decreased the fasting blood glucose level, concomitant use of BBG9-1 and voglibose significantly reduced the fasting blood glucose level. As FIG. 2 clearly shows, although neither BBG9-1 alone nor voglibose alone inhibited the increase in the blood glucose level, concomitant use of BBG9-1 and voglibose synergistically kept the blood glucose level after glucose loading relatively low. Further, as FIG. 3 shows, concomitant use of BBG9-1 and voglibose significantly reduced the AUC as compared with BBG9-1 alone and voglibose alone. That is, concomitant use of BBG9-1 and voglibose synergistically and more strongly improved the glucose tolerance of KK-$A^y$ mice as compared with BBG9-1 alone and voglibose alone.

Use of bifidobacteria other than BBG9-1, lactic acid bacteria, saccharifying bacteria, or butyric acid bacteria in Example 2 leads to the same results as above.

FIGS. 1 to 3 will be described in detail.

FIG. 1 shows the mean±standard error (SE) of 8 individuals of each group. The white bar represents mice fed with CE-2 containing 10% dextrin (Group A). The gray bar represents mice fed with CE-2 containing 10% BBG9-1 dried bacterial cells ($3.4 \times 10^{11}$/g) obtained by the method of Example 1 (Group B). The shaded bar represents mice fed with CE-2 containing 0.0003% voglibose and 10% dextrin (Group C). The black bar represents mice fed with CE-2 containing 10% BBG9-1 dried bacterial cells ($3.4 \times 10^{11}$/g) obtained by the method of Example 1 and 0.0003% voglibose (Group D). * and # represent the significant difference from the mice fed with CE-2 containing 10% dextrin (Group A) (**: $p<0.01$) and the significant difference from the mice fed with CE-2 containing 10% BBG9-1 dried bacterial cells ($3.4 \times 10^{11}$/g) obtained by the method of Example 1 (Group B) (#: $p<0.05$), respectively.

FIG. 2 shows the mean±standard error (SE) of 8 individuals of each group. White circles in the line graph represent mice fed with CE-2 containing 10% dextrin (Group A). White squares represent mice fed with CE-2 containing 10% BBG9-1 dried bacterial cells ($3.4 \times 10^{11}$/g) obtained by the method of Example 1 (Group B). White triangles represent mice fed with CE-2 containing 10% dextrin and 0.0003% voglibose (Group C). Black squares represent mice fed with CE-2 containing 10% BBG9-1 dried bacterial cells ($3.4 \times 10^{11}$/g) obtained by the method of Example 1 and 0.0003% voglibose (Group D).

FIG. 3 shows the mean AUC± standard error (SE) of 8 individuals of each group. The white bar represents mice fed with CE-2 containing 10% dextrin (Group A). The gray bar represents mice fed with CE-2 containing 10% BBG9-1 dried bacterial cells ($3.4 \times 10^{11}$/g) obtained by the method of Example 1 (Group B). The shaded bar represents mice fed with CE-2 containing 0.0003% voglibose and 10% dextrin (Group C). The black bar represents mice fed with CE-2 containing 10% BBG9-1 dried bacterial cells ($3.4 \times 10^{11}$/g) obtained by the method of Example 1 and 0.0003% voglibose (Group D). * and # represent the significant difference from the mice fed with CE-2 containing 10% dextrin (Group A) (**: $p<0.01$) and the significant difference from the mice fed with CE-2 containing 10% BBG9-1 dried bacterial cells ($3.4 \times 10^{11}$/g) obtained by the method of Example 1 (Group B) (#: $p<0.05$), respectively.

In Example 2, while 6-week dietary administration (0.0003%: 0.6 mg/kg·day) of voglibose to KK-A$^y$ mice did not improve the glucose tolerance, 6-week administration of the diet to which at least one kind of bacteria selected from the group consisting of bifidobacteria, lactic acid bacteria, saccharifying bacteria, and butyric acid bacteria was added improved the glucose tolerance. According to "Development of BASEN Tablets (trade name) 3. Effects on insulin secretion and pancreatic islet lesions" by Takeda Pharmaceutical Company Ltd. (www2.takedamed.com/content/search/doc1/067/kaihatsu/kai067_4.html), 9-week dietary administration (0.005%: 4.1 mg/kg·day) of voglibose, which is an α-glucosidase inhibitor, to GK rats characterized by abnormal glucose tolerance improved the glucose tolerance. The results in Example 2 show that concomitant administration of an α-glucosidase inhibitor and bacteria, such as bifidobacteria, is more effective, even when a reduced amount of the α-glucosidase inhibitor is administered for a shorter period, in achieving hypoglycemic effect than single-substance administration of the α-glucosidase inhibitor.

Example 3

Preparation of a Dried Product of Lactic Acid Bacterial Cells, and Measurement of the Viable Cell Count in the Dried Bacterial Cell Product 1. Preparation Method of Bacteria (3B: *Streptococcus faecalis* 129 BIO 3B)

Preparation of a dried product of bacterial cells 3B was performed as follows. A cryopreserved strain of 3B (preserved by Biofermin Pharmaceutical Co., Ltd.) was statically cultured at 37° C. for 24 hours. Then, into 100 parts of liquid medium (2) for the test of lactomin (described in the section "Lactomin" of the Japanese Pharmaceutical Codex), 1 part (volume ratio) of the cultured bacterial cell fluid was inoculated and statically cultured at 37° C. for 18 hours. The obtained culture fluid was centrifuged and bacterial cells were washed with water 3 times. To this, an appropriate amount of water was added. Then, to 1 kg of the wet bacterial cells, 0.1 kg of glutamate and 0.5 kg of dextrin were added. With use of a spray dryer, a dried product of the bacterial cells was obtained. The 3B strain is an ingredient contained in an ethical drug, Biofermin (trade name, made by Biofermin Pharmaceutical Co., Ltd.) etc., and therefore is available from a powder or the like of Biofermin by a conventional purification method.

The above-mentioned liquid medium (2) for the test of lactomin was prepared according to the method described in the section "Lactomin" of the Japanese Pharmaceutical Codex. That is, the following ingredients were mixed and sterilized by heat at 121° C. for 15 minutes with use of a high-pressure steam sterilizer.

| | |
|---|---|
| Yeast extract | 5 g |
| Peptone from casein | 20 g |
| Glucose | 20 g |
| Meat extract | 15 g |
| Tomato juice* | 200 mL |
| Polysorbate 80 | 3 g |
| L-cysteine hydrochloride | 1 g |
| Purified water | 800 mL |
| pH | 6.8 ± 0.1 |

The tomato juice* was prepared by addition of an equivalent amount of purified water to tomato juice, boiling with occasional stirring, pH adjustment to 6.8, and subsequent purification.

2. Measurement of Viable Cell Count in the Dried Bacterial Cell Product

The viable cell count was measured according to the quantitative determination method for lactomin described in the section "Lactomin" of the Japanese Pharmaceutical Codex. That is, precisely weighed 5 g of the dried bacterial cell product was added to 30 mL of the diluent (2), and the mixture was shaken vigorously. The diluent (2) was further added until the total volume reached exactly 50 mL, and then the mixture was shaken well again. 10-fold dilution, where precisely measured 1 mL of the bacterial cell fluid was added to precisely dispensed 9 mL of the diluent (2), was repeated so that the viable cell count was reduced to 20 to 200 cells/mL. Into a Petri dish on which 1 mL of the diluted fluid was placed, 20 mL of the agar medium (2) for the test of lactomin kept at 50° C. was added, and quickly mixed for solidification. After aerobic culture at 37° C. for 24 to 72 hours, the colonies appeared were counted. The viable cell count in the dried bacterial cell product was calculated based on the colony count and the dilution ratio. The viable cell count in the dried bacterial cell product obtained in above 1. was $7.0 \times 10^{11}$ CFU/g.

The above-mentioned agar medium (2) for the test of lactomin was prepared according to the method described in the section "Lactomin" of the Japanese Pharmaceutical Codex. That is, 15 g of agar was added to the above-described liquid medium (2) for the test of lactomin and the mixture was sterilized by heat at 121° C. for 15 minutes with use of a high-pressure steam sterilizer.

Example 4

Preparation of a Dried Product of Saccharifying Bacterial Cells, and Measurement of the Viable Cell Count in the Dried Bacterial Cell Product 1. Preparation Method of Bacteria (H(α): *Bacillus subtilis* 129 BIO H(α))

Preparation of a dried product of bacterial cells H(α) was performed as follows. A preserved strain of H(α) (preserved by Biofermin Pharmaceutical Co., Ltd.) was suspended in sterile physiological saline. Then, into 70 parts of agar medium (2) for the test of saccharifying bacteria (described in the section "Saccharifying bacteria" of the Japanese Pharmaceutical Codex), 2 parts (volume ratio) of the bacterial suspension was inoculated and statically cultured at 37° C. for 72 hours. The culture medium was washed with 18 parts (relative to 70 parts of the medium (volume ratio)) of sterile physiological saline, and obtained bacterial suspension was sieved. With 1 L of the bacterial suspension, 5 kg of starch was mixed, and the mixture was sieved. With this, additional 5 kg of starch was mixed to give a dried bacterial cell product. The saccharifying bacteria H(α) strain is an ingredient contained in an ethical drug, Biofermin (trade name, made by Biofermin Pharmaceutical Co., Ltd.), and therefore is available from a Biofermin powder by a conventional purification method.

The above-mentioned agar medium (2) for the test of saccharifying bacteria was prepared according to the method described in the section "Saccharifying bacteria" of the Japanese Pharmaceutical Codex. That is, the following ingredients were mixed and sterilized by heat at 121° C. for 20 minutes with use of a high-pressure steam sterilizer.

| Meat extract | 7.5 g |
| Peptone from casein | 10 g |
| Sodium chloride | 2.5 g |
| Agar | 15 g |
| Purified water | 1000 mL |
| pH | 7.0 ± 0.1 |

2. Measurement of Viable Cell Count in the Dried Bacterial Cell Product

The viable cell count was measured according to the quantitative determination method for saccharifying bacteria described in the section "Saccharifying bacteria" of the Japanese Pharmaceutical Codex. That is, precisely weighed 5 g of the dried bacterial cell product was added to 30 mL of the diluent, and the mixture was shaken vigorously. The diluent was further added until the total volume reached exactly 50 mL, and then the mixture was shaken well again. 10-fold dilution, where precisely measured 1 mL of the bacterial cell fluid was added to precisely dispensed 9 mL of the diluent, was repeated so that the viable cell count was reduced to 30 to 300 cells/mL. Into a Petri dish on which 1 mL of the diluted fluid was placed, 20 mL of the agar medium (2) for the test of saccharifying bacteria kept at 50° C. was added, and quickly mixed for solidification. After aerobic culture at 37° C. for 24 to 48 hours, the colonies appeared were counted. The viable cell count in the dried bacterial cell product was calculated based on the colony count and the dilution ratio. The viable cell count in the dried bacterial cell product obtained in above 1. was $1.2 \times 10^8$ CFU/g.

The above-mentioned diluent was prepared according to the method described in the section "Saccharifying bacteria" of the Japanese Pharmaceutical Codex. That is, the following ingredients were mixed and sterilized by heat at 121° C. for 20 minutes with use of a high-pressure steam sterilizer.

Diluent

| Peptone from casein | 1 g |
| Sodium chloride | 5 g |
| Purified water | 1000 mL |
| pH | 7.0 ± 0.1 |

Example 5

Hypoglycemic Activity Enhancement by Concomitant Use of Lactic Acid Bacteria, Saccharifying Bacteria, and an α-Glucosidase Inhibitor The 3B obtained by the method of Example 3 as lactic acid bacteria, the H(α) obtained by the method of Example 4 as saccharifying bacteria, and acarbose as an α-glucosidase inhibitor were used. As the acarbose, 100 mg of Glucobay (registered trade name) tablets (made by Bayer Yakuhin, Ltd.) was crushed and used.

Female KK-A$^y$ mice (strain name KK-A$^y$/TaJcl) at 8 weeks old were purchased (from CLEA Japan, Inc.) and preliminarily reared in separate cages for 3 weeks. In the preliminary rearing, free access to a commercial powder diet (trade name: CE-2, made by CLEA Japan, Inc.) and tap water was provided. On the first day of the experiment, the oral glucose tolerance test (OGTT) was conducted. That is, to the mice fasted from the previous day, a glucose solution ((2 g in 5 mL)/kg) was orally administered. Before and 15, 30, 60, and 120 minutes after the administration, the blood was made to leak from a caudal vein, and the glucose concentration in the blood was measured with use of a commercial blood glucose meter for self-check (trade name: Accu-Check Aviva, made by Roche Diagnostics). The area under the blood concentration-time curve (AUC) was calculated, and based on the AUC, the mice were divided into the following 4 groups E to H (7 mice/group). The grouped mice were given free access to the test diet.

Group E: a group fed with CE-2 containing 10% dextrin.

Group F: a group fed with CE-2 containing 5% 3B dried bacterial cells ($7.0 \times 10^{11}$/g) obtained by the method of Example 3 and 5% H(α) dried bacterial cells ($1.2 \times 10^8$/g) obtained by the method of Example 4.

Group G: a group fed with CE-2 containing 0.1% acarbose and 10% dextrin.

Group H: a group fed with CE-2 containing 5% 3B dried bacterial cells ($7.0 \times 10^{11}$/g) obtained by the method of Example 3, 5% H(α) dried bacterial cells ($1.2 \times 10^8$/g) obtained by the method of Example 4, and 0.1 acarbose.

After the test diet was fed to each group for 4 weeks as above, OGTT was conducted for evaluation of glucose tolerance improving activity. The significant difference of each group from Group E was evaluated using Dunnett's test, and the significant difference between 2 groups was evaluated using t-test.

(Results)

Figure 5:
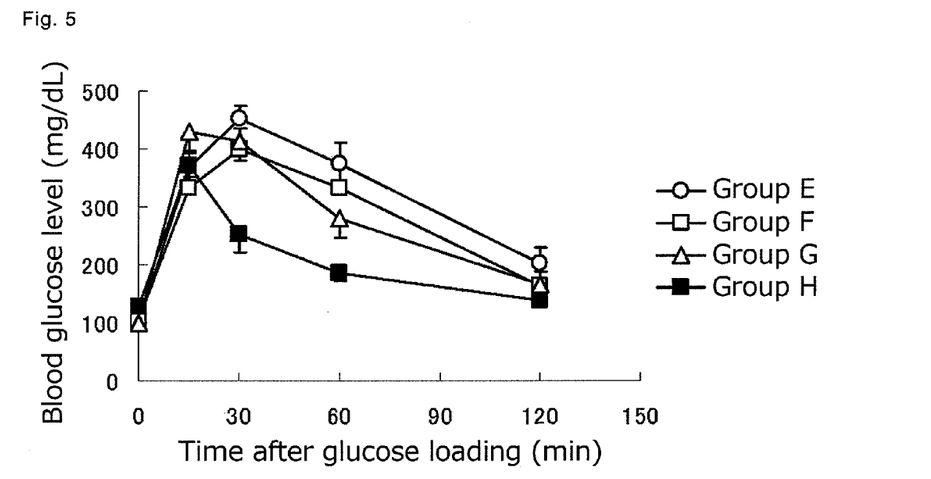
FIG. 5 shows the inhibitory effect of the hypoglycemic effect enhancer of the present invention against increase in the blood glucose level of diabetic model mice after glucose loading.
Figure 6:
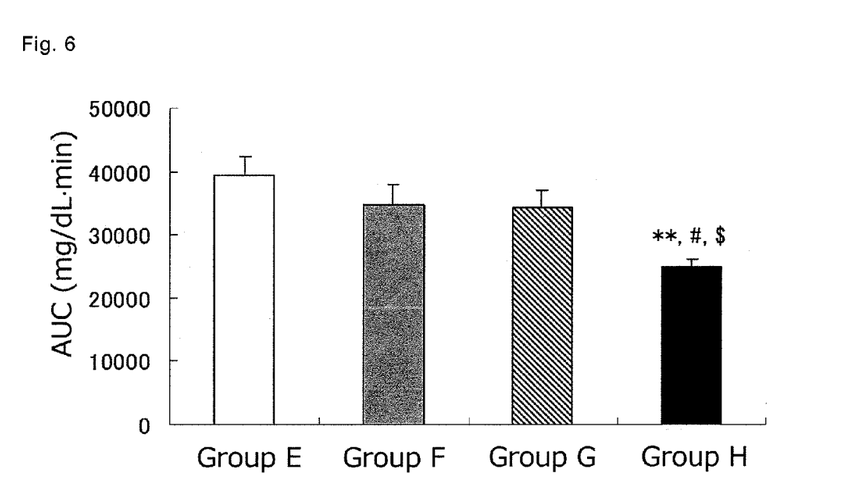
FIG. 6 shows the inhibitory effect of the hypoglycemic effect enhancer of the present invention against increase in the blood glucose level of diabetic model mice after glucose loading, using the area under the blood concentration-time curve (AUC) as an indicator.

FIG. 5 shows the blood glucose levels in the OGTT after 4-week feeding of the test diet to Group E to H mice, and FIG. 6 shows the AUC in the same conditions. As FIG. 5 clearly shows, although neither concomitant use of 3B and H($\alpha$) nor acarbose alone inhibited the increase in the blood glucose level, concomitant use of 3B, H($\alpha$), and acarbose (Group H) synergistically kept the blood glucose level after glucose loading relatively low. Further, as FIG. 6 shows, although neither concomitant use of 3B and H($\alpha$) nor acarbose alone significantly reduced the AUC as compared with Group E, concomitant use of 3B, H($\alpha$), and acarbose (Group H) significantly reduced the AUC. Further, concomitant use of 3B, H($\alpha$), and acarbose significantly reduced the AUC as compared with concomitant use of 3B and H($\alpha$) and with acarbose alone. That is, concomitant use of 3B, H($\alpha$), and acarbose synergistically and more strongly improved the glucose tolerance of KK-A$^y$ mice as compared with concomitant use of 3B and H($\alpha$) and with acarbose alone. Use of 3B and acarbose, or H($\alpha$) and acarbose in Example 5 leads to the same results as in concomitant use of 3B, H($\alpha$), and acarbose (Group H). Use of lactic acid bacteria other than 3B and of saccharifying bacteria other than H($\alpha$) leads to the same results as above.

FIGS. 5 and 6 will be described in detail.

FIG. 5 shows the mean±standard error (SE) of 7 individuals of each group. White circles in the line graph represent mice fed with CE-2 containing 10% dextrin (Group E). White squares represent mice fed with CE-2 containing 5% 3B dried bacterial cells ($7.0 \times 10^{11}$/g) obtained by the method of Example 3 and 5% H($\alpha$) dried bacterial cells ($1.2 \times 10^8$/g) obtained by the method of Example 4 (Group F). White triangles represent mice fed with CE-2 containing 0.1% acarbose and 10% dextrin (Group G). Black squares represent mice fed with CE-2 containing 5% 3B dried bacterial cells ($7.0 \times 10^{11}$/g) obtained by the method of Example 3, 5% H($\alpha$) dried bacterial cells ($1.2 \times 10^8$/g) obtained by the method of Example 4, and 0.1% acarbose (Group H).

FIG. 6 shows the mean AUC±standard error (SE) of 7 individuals of each group. The white bar represents mice fed with CE-2 containing 10% dextrin (Group E). The gray bar represents mice fed with CE-2 containing 5% 3B dried bacterial cells ($7.0 \times 10^{11}$/g) obtained by the method of Example 3 and 5% H($\alpha$) dried bacterial cells ($1.2 \times 10^8$/g) obtained by the method of Example 4 (Group F). The shaded bar represents mice fed with CE-2 containing 0.1% acarbose and 10% dextrin (Group G). The black bar represents mice fed with CE-2 containing 5% 3B dried bacterial cells ($7.0 \times 10^{11}$/g) obtained by the method of Example 3, 5% H($\alpha$) dried bacterial cells ($1.2 \times 10^8$/g) obtained by the method of Example 4, and 0.1% acarbose (Group H). *, #, and $ represent the significant difference from the mice fed with CE-2 containing 10% dextrin (Group E) (**: $p<0.01$), the significant difference from the mice fed with CE-2 containing 5% 3B dried bacterial cells ($7.0 \times 10^{11}$/g) obtained by the method of Example 3 and 5% H($\alpha$) dried bacterial cells ($1.2 \times 10^8$/g) obtained by the method of Example 4 (Group F) (#: $p<0.05$), and the significant difference from the mice fed with CE-2 containing 0.1% acarbose and 10% dextrin (Group G) ($: $p<0.05$), respectively.

Example 6

Hypoglycemic Activity Enhancement by Concomitant Use of Bifidobacteria and an $\alpha$-Glucosidase Inhibitor The BBG9-1 obtained by the method of Example 1 was used as bifidobacteria and acarbose was used as the $\alpha$-glucosidase inhibitor. As the acarbose, 100 mg of Glucobay (registered trade name) tablets (made by Bayer Yakuhin, Ltd.) was crushed and used.

Female KK-A$^y$ mice (strain name KK-A$^y$/TaJcl) at 8 weeks old were purchased (from CLEA Japan, Inc.) and preliminarily reared in separate cages for 2 weeks. In the preliminary rearing, free access to a commercial powder diet (trade name: CE-2, made by CLEA Japan, Inc.) and tap water was provided. On the first day of the experiment, the oral glucose tolerance test (OGTT) was conducted. That is, to the mice fasted from the previous day, a glucose solution ((2 g in 5 mL)/kg) was orally administered. Before and 15, 30, 60, and 120 minutes after the administration, the blood was made to leak from a caudal vein, and the glucose concentration in the blood was measured with use of a commercial blood glucose meter for self-check (trade name: Accu-Check Aviva, made by Roche Diagnostics). The area under the blood concentration-time curve (AUC) was calculated, and based on the AUC, the mice were divided into the following 4 groups I to L (9 mice/group). The grouped mice were given free access to the test diet.

Group I: a group fed with CE-2 containing 10% dextrin.
Group J: a group fed with CE-2 containing 10% BBG9-1 dried bacterial cells ($3.4 \times 10^{11}$/g) obtained by the method of Example 1.
Group K: a group fed with CE-2 containing 0.1% acarbose and 10% dextrin.
Group L: a group fed with CE-2 containing 10% BBG9-1 dried bacterial cells ($3.4 \times 10^{11}$/g) obtained by the method of Example 1 and 0.1% acarbose.

After the test diet was fed to each group for 4 weeks as above, OGTT was conducted for evaluation of glucose tolerance improving activity. The significant difference of each group from Group I was evaluated using Dunnett's test, and the significant difference between 2 groups was evaluated using t-test.

(Results)

Figure 7:
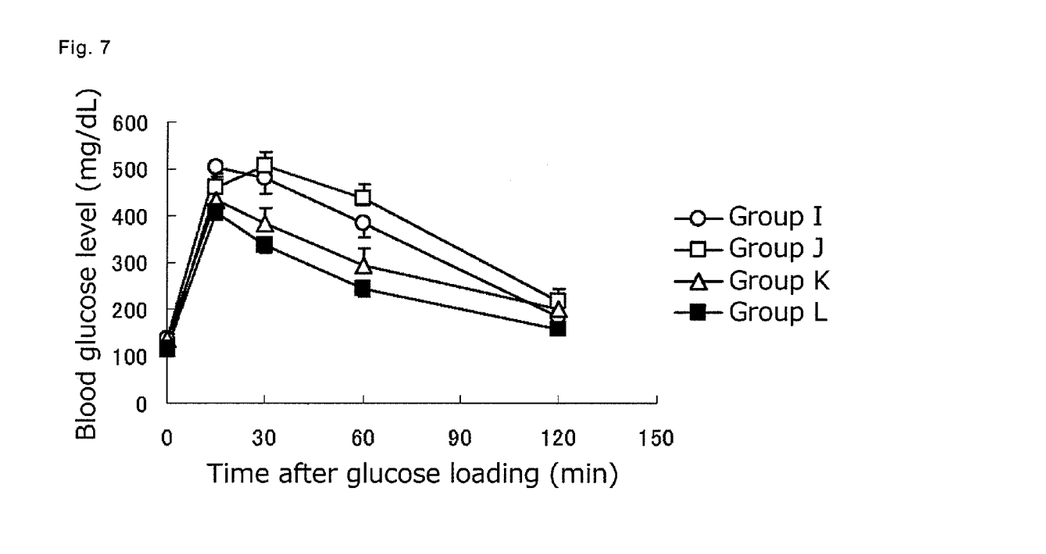
FIG. 7 shows the inhibitory effect of the hypoglycemic effect enhancer of the present invention against increase in the blood glucose level of diabetic model mice after glucose loading.
Figure 8:
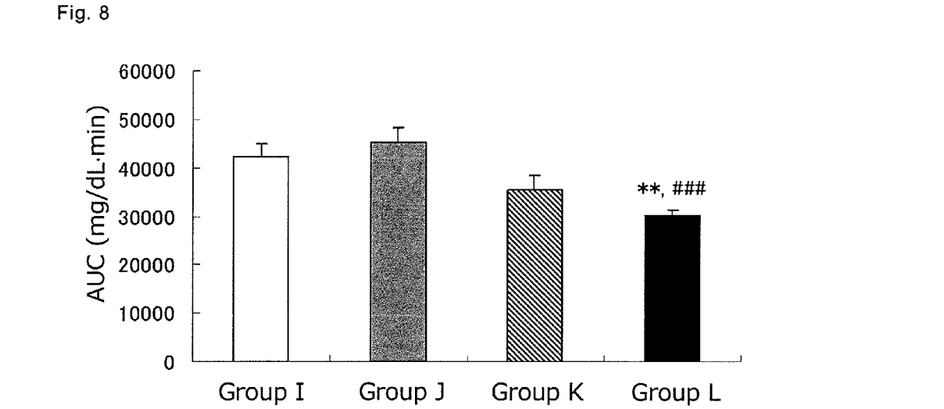
FIG. 8 shows the inhibitory effect of the hypoglycemic effect enhancer of the present invention against increase in the blood glucose level of diabetic model mice after glucose loading, using the area under the blood concentration-time curve (AUC) as an indicator.

FIG. 7 shows the blood glucose levels in the OGTT after 4-week feeding of the test diet to Group I to L mice, and FIG. 8 shows the AUC in the same conditions. As FIG. 7 clearly shows, although neither BBG9-1 alone nor acarbose alone inhibited the increase in the blood glucose level, concomitant use of BBG9-1 and voglibose synergistically kept the blood glucose level after glucose loading relatively low. Further, as FIG. 8 shows, although neither BBG9-1 alone nor acarbose alone significantly reduced the AUC as compared with Group I, concomitant use of BBG9-1 and acarbose significantly reduced the AUC. Further, concomitant use of BBG9-1 and acarbose significantly reduced the AUC as compared with BBG9-1 alone. That is, concomitant use of BBG9-1 and acarbose synergistically and more strongly improved the glucose tolerance of KK-A$^y$ mice as compared with BBG9-1 alone and with acarbose alone. Use of bifidobacteria other than BBG9-1, lactic acid bacteria, saccharifying bacteria, or butyric acid bacteria in Example 6 leads to the same results as above.

FIGS. 7 and 8 will be described in detail.

FIG. 7 shows the mean±standard error (SE) of 9 individuals of each group. White circles in the line graph represent mice fed with CE-2 containing 10% dextrin (Group I). White squares represent mice fed with CE-2 containing 10% BBG9-1 dried bacterial cells ($3.4 \times 10^{11}$/g) obtained by the method of Example 1 (Group J). White triangles represent mice fed with CE-2 containing 0.1% acarbose and 10% dextrin (Group K). Black squares represent mice fed with CE-2 containing 10% BBG9-1 dried bacterial cells ($3.4 \times 10^{11}$/g) obtained by the method of Example 1 and 0.1% acarbose (Group L).

FIG. 8 shows the mean AUC±standard error (SE) of 9 individuals of each group. The white bar represents mice fed with CE-2 containing 10% dextrin (Group I). The gray bar represents mice fed with CE-2 containing 10% BBG9-1 dried bacterial cells ($3.4 \times 10^{11}$/g) obtained by the method of Example 1 (Group J). The shaded bar represents mice fed with CE-2 containing 0.1% acarbose and 10% dextrin (Group K). The black bar represents mice fed with CE-2 containing 10% BBG9-1 dried bacterial cells ($3.4 \times 10^{11}$/g) obtained by the method of Example 1 and 0.1% acarbose (Group L). * and # represent the significant difference from the mice fed with CE-2 containing 10% dextrin (Group I) (**: $p<0.01$) and the significant difference from the mice fed with CE-2 containing 10% BBG9-1 dried bacterial cells ($3.4 \times 10^{11}$/g) obtained by the method of Example 1 (Group J) (###: $p<0.001$), respectively.

INDUSTRIAL APPLICABILITY

The hypoglycemic effect enhancer of the present invention is useful for prevention or improvement of lifestyle-related diseases, such as diabetes and obesity.

REFERENCE SIGNS LIST 1, 2 Gas channels wherethrough a compressed gas is supplied
3, 4 Liquid channels wherethrough a liquid containing a substance to be dried is supplied
5 Fluid flow surface
6 Collision focal spot
7 Sprayed droplets

The invention claimed is:

1. A method for enhancing the hypoglycemic activity of voglibose, the method comprising administering to a patient in need thereof lactic acid bacteria, and saccharifying bacteria or bifidobacteria in combination with voglibose, and enhancing the hypoglycemic activity of voglibose.

2. A method for enhancing the hypoglycemic activity of lactic acid bacteria, and saccharifying bacteria or bifidobacteria, the method comprising administering to a patient in need thereof voglibose in combination with the bacteria, and enhancing the hypoglycemic activity of the bacteria.

3. A method for promoting the expression of the hypoglycemic activity of voglibose, the method comprising administering to a patient in need thereof lactic acid bacteria, and saccharifying bacteria or bifidobacteria in combination with voglibose, and promoting the expression of the hypoglycemic activity of voglibose.

* * * * *